(12) United States Patent
Kino et al.

(10) Patent No.: US 8,858,944 B2
(45) Date of Patent: Oct. 14, 2014

(54) TREATMENT DRUG FOR AUTOIMMUNE DISEASES AND ALLERGIC DISEASES

(75) Inventors: Koichi Kino, Osaka (JP); Toshihiro Kai, Osaka (JP); Mitsuhiro Matsumoto, Osaka (JP); Masunori Kajikawa, Nagano (JP); Masahito Sugiura, Nagano (JP); Emi Shimizu, Nagano (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 13/701,408

(22) PCT Filed: Jun. 2, 2011

(86) PCT No.: PCT/JP2011/062741
§ 371 (c)(1),
(2), (4) Date: Jan. 29, 2013

(87) PCT Pub. No.: WO2011/152503
PCT Pub. Date: Dec. 8, 2011

(65) Prior Publication Data
US 2013/0121914 A1 May 16, 2013

(30) Foreign Application Priority Data
Jun. 2, 2010 (JP) ................................ 2010-127316

(51) Int. Cl.
*A61K 39/395* (2006.01)
*G01N 33/68* (2006.01)
*G01N 33/50* (2006.01)
*C12Q 1/68* (2006.01)
*C07K 16/28* (2006.01)
*A61K 39/00* (2006.01)

(52) U.S. Cl.
CPC .. *A61K 39/39533* (2013.01); *G01N 2333/4703* (2013.01); *G01N 33/6893* (2013.01); *G01N 33/505* (2013.01); *C12Q 1/6888* (2013.01); *A61K 2039/505* (2013.01); *C07K 16/2803* (2013.01)
USPC ..................................... 424/143.1

(58) Field of Classification Search
None
See application file for complete search history.

(56) References Cited

U.S. PATENT DOCUMENTS

| | | | |
|---|---|---|---|
| 2002/0187526 A1* | 12/2002 | Ruben et al. ................. | 435/69.5 |
| 2007/0184444 A1 | 8/2007 | Abbas et al. | |
| 2010/0034817 A1 | 2/2010 | Abbas et al. | |
| 2010/0151000 A1 | 6/2010 | Thomas et al. | |
| 2011/0136113 A1 | 6/2011 | Uga et al. | |

FOREIGN PATENT DOCUMENTS

| | | |
|---|---|---|
| CN | 101646418 A | 2/2010 |
| EP | 1811041 A1 | 7/2007 |
| JP | 3023467 B2 | 1/2000 |
| WO | WO 2005/016962 A2 | 2/2005 |
| WO | WO 2005/019258 A2 | 3/2005 |
| WO | WO 2008/063776 A2 | 5/2008 |
| WO | WO 2008/106131 A2 | 9/2008 |
| WO | WO 2009/092087 A2 | 7/2009 |
| WO | WO 2010/017468 A1 | 2/2010 |
| WO | WO 2010/024289 A1 | 3/2010 |

OTHER PUBLICATIONS

Ooi et al. (Nephrology 15 (2010) 513-521).*
Steinman, J. Exp. Med., vol. 205, No. 7, 1517-1522 (2008).*
O'Connor et al., Nat Immunol. Jun. 2009;10(6):603-9.*
Ogawa et al., Clin Immunol. Jan. 2004;110(1):55-62.*
Hueber et al., European Crohn's and Colitis Organisation, Congress Abstrct 2012, pp. 1-2.*
Hartmann et al., *Inflamm. Research*, 55: 322-334 (2006).
Hirota et al., *Semin. Immunopathol.*, 32: 3-16 (2010).
Kroenke et al., *J. Exp. Med.*, 205: 1535-1541 (2008).
Romagnani et al., *Molecular Immunology*, 47: 3-7 (2009).
Zhang et al., *Clinical Neurology and Neurosurgery*, 112: 641-645 (2010).
European Patent Office, Extended European Search Report in European Patent Application No. 11789905.4 (Oct. 23, 2013).
Chiang et al., *Nature Medicine*, 15(7): 766-774 (2009).
Crome et al., *Clinical and Experimental Immunology*, 159: 109-119 (2009).
Fan et al., *Develop. Growth Differ.*, 40: 277-286 (1998).
Guenette et al., *Developmental Genetics*, 21: 268-278 (1997).
Huang et al., *Differentiation*, 45: 76-83 (1990).
Ivanov et al., *Cell*, 126: 1121-1133 (2006).
Kallies et al., *Immunity*, 26: 555-566 (2007).
Korn et al., *Annual Review of Immunology.*, 27: 485-517 (2009).
Lain et al., *Journal of Biological Chemistry.*, 284(13): 8930-8939 (2009).
Langrish et al., *Journal of Experimental Medicine*, 201(2): 233-240 (2005).
Louten et al., *Journal of Allergy and Clinical Immunology*, 123(5): 1004-1011 (2009).
Pridans et al., *Journal of Immunology*, 180: 1719-1728 (2008).
Tesmer et al., *Immunological Reviews*, 223: 87-113 (2008).
Webb et al., *Journal of Neuroimmunology*, 153: 108-121 (2004).

(Continued)

*Primary Examiner* — Zachary Skelding
(74) *Attorney, Agent, or Firm* — Leydig, Voit & Mayer, Ltd.

(57) ABSTRACT

The present invention provides an agent for the prophylaxis or therapy of autoimmune diseases or allergic diseases, which contains an anti-Embigin antibody, particularly an anti-Embigin antibody showing cytotoxicity or a cytotoxicity inducing activity, an agent for the prophylaxis or therapy of diseases involving Th17 cell, and a cytotoxic agent to Th17 cell. In addition, an agent for detection of Th17 cell, which contains an anti-Embigin antibody, a convenient detection method of Th17 cell, which uses the agent, a method of efficiently delivering a drug and the like in a Th17 cell selective manner, which uses an anti-Embigin antibody, and a drug delivery system to Th17 cell are provided.

8 Claims, 10 Drawing Sheets

(56) References Cited

OTHER PUBLICATIONS

Japanese Patent Office, International Search Report in International Patent Application No. PCT/JP2011/062741 (Jul. 5, 2011) English translation.

Ezendam et al., *Environmental Health Perspectives*, 112(7): 782-791 (May 2004).
Haywood et al., *The Journal of Immunology*, 167: 1728-1733 (2001).
Chinese Patent Office, First Office Action in Chinese Patent Application No. 201180037505 (Feb. 11, 2014) English translation.

* cited by examiner

- Clone 2G23

- Clone 3E64

B ; brain
H ; heart
SI ; small intestin
K ; kidney
Li ; liver
Lu ; lung
M ; muscle
St ; stomach
Sp ; spleen
Ov ; ovary
Te ; testis

TREATMENT DRUG FOR AUTOIMMUNE DISEASES AND ALLERGIC DISEASES

CROSS-REFERENCE TO RELATED APPLICATIONS

This patent application is the U.S. national phase of International Patent Application No. PCT/JP2011/062741, filed on Jun. 2, 2011, which claims the benefit of Japanese Patent Application No. 2010-127316, filed on Jun. 2, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 9,733 bytes ASCII (Text) file named "711792SequenceListing.txt," created Nov. 30, 2012.

TECHNICAL FIELD

The present invention relates to a therapeutic agent for autoimmune diseases and allergic diseases. More particularly, it relates to a therapeutic agent for the above-mentioned diseases involving Th17 cell, a drug showing cytotoxicity against Th17 cell and the like.

BACKGROUND ART

Helper T cell (hereinafter to be referred to as "Th cell") playing a central role in acquired immunity has been classified into Th1 cell involved in cellular immunity and Th2 cell involved in humoral immunity based on the difference in the cytokines they produce and the like.

In recent years, however, as a new Th cell subset different from Th1 cell and Th2 cell, Th17 cell has been identified as a Th cell that specifically produces IL-17 (non-patent document 1). The Th17 cell has been found to be involved in autoimmune diseases over a wide range such as multiple sclerosis, psoriasis, rheumatism, inflammatory bowel disease and allergic diseases such as contact hypersensitivity, atopic dermatitis and the like and, for example, in multiple sclerosis, it has been found using an animal model that Th17 cell is a stronger pathogenic cell than Th1 cell conventionally considered to be important (non-patent document 1, non-patent document 2, non-patent document 3, non-patent document 4).

Thus, while Th17 cell is drawing attention as a new target of autoimmune diseases, allergic diseases and the like, a drug that acts Th17 cell-selectively has not been developed yet.

For example, attempts have been made to treat autoimmune diseases by non-specifically suppressing lymphocyte infiltration into the lesion by using FTY-720 (fingolimod) and the like. However, discontinuation of medication has been reported to cause immediate aggravation of symptoms (non-patent document 5), and problems still remain.

Different from this approach, a efficacy of therapy has been reported in various autoimmune disease models, which is afforded by eliminating both Th17 cell and Th1 cell from the body by using an antibody having an ADCC activity (anti-lymphotoxin α antibody) (patent document 1). However, since both Th1 cell and Th17 cell are also involved in the biological defense (non-patent document 2, non-patent document 3), non-specific action (FTY-720) or inhibition of functions of both Th1 cell and Th17 cell could excessively decrease the biological defense function. Therefore, a pharmaceutical product that specifically acts on Th17 cell that shows a strong action as a pathogenic cell of autoimmune diseases has been desired.

To develop such a pharmaceutical product, for example, a molecule specifically expressed in Th17 cell may be used as a target. As a molecule specifically expressed in Th17 cell, RORγt which is a nuclear receptor, and the like have been identified (non-patent document 6), but Th17 cell-specific cell surface molecule has not been found (non-patent document 7).

Embigin is known as a single membrane-spanning protein that forms a family with CD147 (Basigin) and neuroplastin.

Embigin has been reported to be expressed in embryonic carcinoma cells (non-patent document 8), mouse fetal stage (early endoderm) (non-patent document 9), rat prostate, mammary gland, heart, liver, lung, brain (non-patent document 10), rat muscle (non-patent document 11), mouse hematopoietic cell (non-patent document 12). In addition, Embigin has been reported to show increased expression in rat hepatic fibrosis model (patent document 2).

Moreover, Embigin has been reported to be one of several thousand genes that vary on stimulation of CDC cell with anti-CD3 antibody/anti-CD28 antibody (patent document 3). However, this report is based on the comparison of a cell induced to differentiate into Th1 cell or Th2 cell and Th0 cell, and provides no description as to how Embigin varied in what cell, and completely no description as to Th17 cell.

PRIOR ART DOCUMENTS

Patent Documents patent document 1: WO2008/063776
patent document 2: EP-A-1811041
patent document 3: WO2005/016962

Non-Patent Documents non-patent document 1: J. Exp. Med. (2005); 201:233-240
non-patent document 2: Immunological Reviews (2008); 223:87-113
non-patent document 3: J. Allergy Clin. Immunol. (2009); 123:1004-1011
non-patent document 4: Clinical and Experimental Immunology (2009); 159:109-119
non-patent document 5: Journal of Neuroimmunology 153 (2004); 108-121
non-patent document 6: Cell (2006); 126:1121-1133
non-patent document 7: Annual Review of Immunology (2008); 27:485-517
non-patent document 8: Differentiation. (1990); 45:76-83
non-patent document 9: Develop. Growth Differ. (1998); 40:277-286
non-patent document 10: Developmental Genetics (1997); 21:268-278
non-patent document 11: J. Biol. Chem. (2009); 284:8930-8939
non-patent document 12: J. Immunology (2008); 180:1719-1728

SUMMARY OF THE INVENTION

Problems to be Solved by the Invention

The problem of the present invention is to provide a therapeutic agent for autoimmune diseases and allergic diseases such as a therapeutic agent for multiple sclerosis and the like and a cytotoxic agent to Th17 cell, which targets Th17 cell. In addition, the problem of the present invention is to find a cell surface molecule that is more selectively expressed in Th17 cell, and provide a drug delivery system (DDS) to deliver a drug to Th17 cell, Th17 cell marker, and a convenient detection method of Th17 cell.

Means of Solving the Problems

The present inventors have conducted intensive studies and found that Embigin is highly expressed on Th17 cell surface, but expressed at an extremely low level in other blood cells including blood-derived cultured cells such as Th1 cell, Th2 cell, Th0 cell, B cell, leukocyte and the like. Furthermore, they have found that, since an anti-Embigin antibody conjugated with a drug showing cytotoxicity selectively decreases or eliminates Th17 cell, and an anti-Embigin antibody having a structure to induce cytotoxicity selectively decreases or eliminates Th17 cell and shows a prophylactic or therapeutic effect for autoimmune disease model animals, an anti-Embigin antibody conjugated with a drug showing cytotoxicity and an anti-Embigin antibody having a structure to induce cytotoxicity are useful for autoimmune diseases and allergic diseases, particularly multiple sclerosis, which resulted in the completion of the present invention.

In addition, they have newly found that, since a drug conjugated with an anti-Embigin antibody reaches Th17 cell efficiently, the anti-Embigin antibody is useful for a drug delivery system that delivers a drug to Th17 cell.

Furthermore, the present inventors have conducted intensive studies of Th17 cell and found that, since Embigin is highly expressed in Th17 cell than in other blood cells, Th17 cell can be conveniently determined by examining the expression of Embigin in blood cells.

Accordingly, the present invention relates to the following.
[1] An agent for the prophylaxis and/or therapy of an autoimmune disease or allergic disease comprising an anti-Embigin antibody.
[2] The agent of [1], wherein the anti-Embigin antibody has a cytotoxicity or a cytotoxicity inducing activity.
[3] The agent of [1], wherein the anti-Embigin antibody has a cytotoxicity inducing activity.
[4] The agent of [3], wherein the anti-Embigin antibody having the cytotoxicity inducing activity has a structure inducing an antibody dependent cellular cytotoxicity (ADCC) and/or a complement dependent cytotoxicity (CDC).
[5] The agent of [3], wherein the subclass of the anti-Embigin antibody having the cytotoxicity inducing activity is IgG1, IgG3 or IgM.
[6] The agent of [1], wherein the anti-Embigin antibody has a cytotoxicity.
[7] The agent of [6], wherein the anti-Embigin antibody having the cytotoxicity is conjugated with a cytotoxic substance, a chemotherapeutic agent or a radioisotope.
[8] The agent of any of [1]-[7], wherein the disease is related to a Th17 cell.
[9] The agent of any of [1]-[7], wherein the disease is multiple sclerosis, psoriasis, rheumatism, inflammatory bowel disease, contact hypersensitivity, steroid-resistant asthma, chronic noninfectious uveitis, chronic obliterative pulmonary diseases, glomerulonephritis or atopic dermatitis.
[10] The agent of any of [1]-[7], wherein the disease is multiple sclerosis.
[11] A cytotoxic agent to a Th17 cell, comprising an anti-Embigin antibody.
[12] The agent of [11], wherein the anti-Embigin antibody has a cytotoxicity or a cytotoxicity inducing activity.
[13] The agent of [11], wherein the anti-Embigin antibody has a cytotoxicity inducing activity.
[14] The agent of [13], wherein the anti-Embigin antibody having the cytotoxicity inducing activity has a structure inducing an antibody dependent cellular cytotoxicity (ADCC) and/or a complement dependent cytotoxicity (CDC).
[15] The agent of [13], wherein the subclass of the anti-Embigin antibody having the cytotoxicity inducing activity is IgG1, IgG3 or IgM.
[16] The agent of [11], wherein the anti-Embigin antibody has a cytotoxicity.
[17] The agent of [16], wherein the anti-Embigin antibody having the cytotoxicity is conjugated with a cytotoxic substance, a chemotherapeutic agent or a radioisotope.
[18] An anti-Embigin antibody for a drug delivery system (DDS), which is used for delivering a drug to a Th17 cell.
[19] The antibody of [18], which is conjugated with the aforementioned drug.
[20] The antibody of [18] or [19], wherein the drug is a cytotoxic substance, a chemotherapeutic agent or a radioisotope.
[21] A drug delivery system for delivering a drug to a Th17 cell, which uses an anti-Embigin antibody.
[22] The drug delivery system of [21], wherein the anti-Embigin antibody is conjugated with the aforementioned drug.
[23] The drug delivery system of [21] or [22], wherein the drug is a cytotoxic substance, a chemotherapeutic agent or a radioisotope.
[24] A reagent for detection of a Th17 cell, comprising an anti-Embigin antibody.
[25] The reagent of [24], wherein the anti-Embigin antibody is labeled with a fluorescent substance or a radioisotope.
[26] A reagent for detection of a Th17 cell, comprising a nucleic acid capable of specifically detecting an Embigin gene transcription product.
[27] A kit for detection of a Th17 cell, comprising the reagent of any of [24]-[26].
[28] A method of detecting a Th17 cell, comprising measuring the expression of Embigin.
[29] The method of [28], comprising measuring the expression of Embigin in a cell obtained from a test animal.
[30] The method of [28] or [29], comprising measuring the expression of Embigin using the reagent of any of [24]-[26].
[31] Use of an Embigin or Embigin gene transcription product as a marker molecule in the detection of a Th17 cell.
[32] A method for the prophylaxis and/or therapy of an autoimmune disease or an allergic disease in a subject, comprising administering an effective amount of the anti-Embigin antibody to the subject.
[33] The method of [32], wherein the anti-Embigin antibody has a cytotoxicity or a cytotoxicity inducing activity.
[34] The method of [32], wherein the anti-Embigin antibody has a cytotoxicity inducing activity.
[35] The method of [34], wherein the anti-Embigin antibody having the cytotoxicity inducing activity has a structure inducing an antibody dependent cellular cytotoxicity (ADCC) and/or a complement dependent cytotoxicity (CDC).

[36] The method of [34], wherein the subclass of the anti-Embigin antibody having a cytotoxicity inducing activity is IgG1, IgG3 or IgM.
[37] The method of [32], wherein the anti-Embigin antibody has a cytotoxicity.
[38] The method of [37], wherein the anti-Embigin antibody having the cytotoxicity is conjugated with a cytotoxic substance, a chemotherapeutic agent or a radioisotope.
[39] The method of any of [32]-[38], wherein the disease is related to a Th17 cell.
[40] The method of any of [32]-[38], wherein the disease is multiple sclerosis, psoriasis, rheumatism, inflammatory bowel disease, contact hypersensitivity, steroid-resistant asthma, chronic noninfectious uveitis, chronic obliterative pulmonary disease, glomerulonephritis or atopic dermatitis.
[41] The method of any of [32]-[38], wherein the disease is multiple sclerosis.
[42] A method for inducing a cellular damage in a Th17 cell, comprising contacting an anti-Embigin antibody to the Th17 is cell.
[43] The method of [42], wherein the anti-Embigin antibody has a cytotoxicity or a cytotoxicity inducing activity.
[44] The method of [42], wherein the anti-Embigin antibody has a cytotoxicity inducing activity.
[45] The method of [44], wherein the anti-Embigin antibody having a cytotoxicity inducing activity has a structure inducing an antibody dependent cellular cytotoxicity (ADCC) and/or a complement dependent cytotoxicity (CDC).
[46] The method of [44], wherein the subclass of the anti-Embigin antibody having the cytotoxicity inducing activity is IgG1, IgG3 or IgM.
[47] The method of [42], wherein the anti-Embigin antibody has a cytotoxicity.
[48] The method of [47], wherein the anti-Embigin antibody having the cytotoxicity is conjugated with a cytotoxic substance, a chemotherapeutic agent or a radioisotope.
[49] The method of any of [42]-[48], comprising contacting an anti-Embigin antibody to a Th17 cell in a subject by administering an effective amount of the anti-Embigin antibody to the subject.

Effect of the Invention

According to the present invention, an agent for the prophylaxis or therapy of autoimmune diseases or allergic diseases, and a cytotoxic agent to a Th17 cell can be provided.
Furthermore, the present invention can provide a drug delivery system for delivering a drug to a Th17 cell, a reagent for detection of a Th17 cell and a detection method of a Th17 cell, which can conveniently detect a Th17 cell.

DESCRIPTION OF EMBODIMENTS

Figure 1:
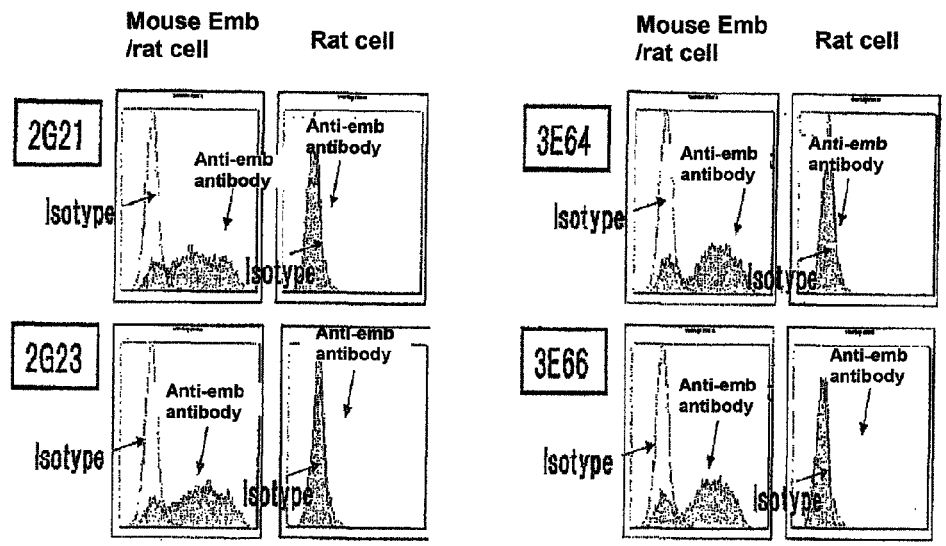
FIG. 1 is a figure showing evaluation of a binding activity of an anti-Embigin antibody to mouse Embigin expressing rat cells and rat cells by flow cytometry. Isotype (rat IgG) relative to the anti-Embigin antibody was 5 μg/mL concentration, and a culture supernatant was used as the anti-Embigin antibody (anti-emb antibody).

The present invention is explained in detail in the following.

1. Anti-Embigin Antibody in the Present Invention

Embigin is a single membrane-spanning protein forming a family with CD147 (Basigin) and neuroplastin. Embigin is known to have amino acid sequences of, for example, human Embigin (NCBI database accession number: NP_940851, SEQ ID NO: 1), rat Embigin (same accession number: NP_446171) or mouse Embigin (same accession number: NP_034460, SEQ ID NO: 8).

As the nucleic acid sequence of a gene encoding Embigin (hereinafter referred to as "Embigin gene"), for example, human Embigin gene (same accession number: NM_198449, SEQ ID NO: 2) or mouse Embigin gene (same accession number: NM_010330, SEQ ID NO: 9) are also known.

Embigin in the present specification encompasses not only "protein" or "(poly)peptide" shown by these known sequences, but also, for example, homologs thereof (homologs and splice variants), variants, derivatives, mature forms, amino acid-modified forms and the like as long as they have biological functions equivalent to those of a particular amino acid sequence showing human Embigin. Here, examples of the homolog include proteins of other biological species such as mouse, rat and the like, which correspond to human protein. They can be deductively identified from the base sequence of a gene identified by HomoloGene (http://www.ncbi.nlm.nih.gov/HomoloGene/). In addition, the variant encompasses naturally-occurring allele variants, variants not present in nature, and variants having amino acid sequences artificially altered by deleting, substituting, adding or inserting. Examples of the above-mentioned variant include those having at least 70%, preferably 80%, more preferably 95%, further more preferably 97%, homology with a mutation-free protein or (poly)peptide. In addition, the amino acid-modified form encompasses naturally-occurring amino acid-modified forms and amino acid-modified forms not present in nature, and amino acid-phosphorylated forms can be specifically mentioned.

The anti-Embigin antibody in the present invention may be any as long as it specifically recognizes Embigin. The "specifically recognizes" means to specifically bind to Embigin. Specifically, it may be an antibody capable of specifically recognizing an expression product (protein) of Embigin gene (hereinafter also referred to as "Embigin" in the present specification), and an antibody capable of recognizing an extracellular region of Embigin (32nd to 257th of the amino acid sequence shown by SEQ ID NO: 1) is preferable.

The above-mentioned antibody to be used in the present invention includes polyclonal and monoclonal antibodies. Depending on the type of constant domain of heavy chain, the antibody is divided into 5 major classes: IgA, IgD, IgE, IgG and IgM. Of these, some antibodies are further divided into subclass or isotype (for example, IgG1, IgG2, IgG3, IgG4 etc. in the case of IgG).

The antibody includes human antibody, chimeric antibody, humanized antibody, single strand antibody, Fab fragment or fragments produced by Fab expression library, small antibody (also including antibody fragment), polyspecific antibody and the like, and further, modified antibodies such as an antibody conjugated with a drug and the like. Furthermore, a part of the above-mentioned antibody having an antigen binding property, an antibody with enhanced cytotoxicity inducing activity, a bispecific antibody, an antibody fused with a protein and the like are also encompassed.

As the anti-Embigin antibody to be used in the present invention, for example, commercially available anti-Embigin antibodies (manufactured by Santa Cruz, manufactured by eBioscience etc.) may be used, or it may be a polyclonal or monoclonal antibody produced using a known means.

As the anti-Embigin antibody to be used in the present invention, a monoclonal antibody and a polyclonal antibody derived from mammals are particularly preferable. The monoclonal antibody and polyclonal antibody can be produced by a known method for those of ordinary skill in the art.

Examples of the monoclonal antibody and polyclonal antibody derived from mammals include those produced in the blood of animal, those produced by hybridomas, those produced by a host transformed with an expression vector containing an antibody gene by a genetic engineering means, those produced in large amounts in a CHO cell factory by the gene of an optimal antibody screened for from an enormous clone library containing 1,000,000,000,000 molecules by phage display, human antibody directly produced using transgenic mouse that produces human antibody, and the like.

The protein to be used as a sensitizing antigen for obtaining the anti-Embigin antibody of the present invention for the preparation of a polyclonal antibody is not limited by the animal species of its origin such as human, mouse, rat and the like. However, it is preferably determined in consideration of the compatibility with a parent cell to be used for cell fusion, and generally, a protein derived from a mammal is preferable, and a protein derived from human is particularly preferable. It may also be a complete protein or a partial peptide of a protein. For example, when Embigin is human Embigin, a cell that expresses human Embigin protein and human Embigin, a partial peptide of human Embigin and the like can be used. Examples of the partial peptide of a protein include amino (N) terminal fragment and carboxy (C) terminal fragment of a protein. The anti-Embigin antibody in the present invention means an antibody that reacts with a full-length or fragment of Embigin protein.

For example, a polyclonal antibody can be obtained as follows. That is, a natural Embigin protein, or a recombinant Embigin protein expressed as fusion protein with GST by a microorganism such as *Escherichia coli* and the like, or a partial peptide thereof is used for immunizing a small animal such as rabbit and the like to give a serum. This is purified by, for example, ammonium sulfate precipitation, protein A, protein G column, DEAE ion exchange chromatography, affinity column coupled with Embigin protein or synthetic peptide, and the like to give a polyclonal antibody.

An antigen can be prepared according to, for example, a method using baculovirus (e.g., WO98/46777 etc.) and the like. When the antigen has low immunogenicity, it is conjugated with a macromolecule having immunogenicity such as albumin and the like and used for immunization.

As a production method of a monoclonal antibody, an animal is immunized with a sensitizing antigen according to a known method. As a general method, a sensitizing antigen is intraperitoneally or subcutaneously injected to a mammal. To be specific, a sensitizing antigen is diluted with or suspended in PBS (Phosphate-Buffered Saline), saline and the like to an adequate amount, and a suitable amount of a conventional adjuvant, for example, Freund's complete adjuvant, is mixed therewith as desired. The mixture is emulsified and immunized to a mammal several times every 4-21 days. It is also possible to use a suitable carrier for immunization with a sensitizing antigen.

In this way, a mammal is immunized, an increase of a desired antibody level in the serum is confirmed, immune cells are obtained from the mammal and subjected to cell fusion. Particularly preferable examples of the immune cell include splenocytes. As the other parent cell to be fused with the aforementioned immune cell, mammalian myeloma cell is used. As the myeloma cell, various known cell lines, for example, P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), R210 (Galfre, G. et al., Nature (1979) 277, 131-133) and the like are preferably used.

The cell fusion of the aforementioned immune cell and myeloma cell can be basically performed according to a known method, for example, the methods of Kohler, Milstein et al. (Kohler, G. and Milstein, C., Methods Enzymol. (1981) 73, 3-46) and the like.

More specifically, the aforementioned cell fusion is performed, for example, in the presence of a cell fusion promoter in a conventional nutrient culture medium. As the fusion promoter, for example, polyethylene glycol (PEG), Hemagglutinating Virus of Japan (HVJ) and the like are used, and an auxiliary agent such as dimethyl sulfoxide and the like can also be further added for use for enhancing the fusion efficiency when desired.

The ratio of the immune cells and myeloma cells to be used can be optionally determined. For example, the immune cells are preferably used in 1- to 10-fold relative to the myeloma cells. As a culture medium to be used for the aforementioned cell fusion, for example, RPMI1640 culture medium and MEM culture medium preferable for the growth of the aforementioned myeloma cell line, as well as a culture medium generally used for this kind of cell culture can be used, and further, a serum supplement such as fetal bovine serum (FCS) and the like can also be used in combination.

For cell fusion, a given amount of the aforementioned immune cells and myeloma cells are mixed well in the aforementioned culture medium, a PEG solution (e.g., average molecular weight of about 1000-6000) heated to about 37° C. in advance is generally added at 30-60% (w/v) concentration, and the mixture is mixed to form the object hybridoma. Then, an operation of successively adding a suitable culture medium, centrifuging the mixture and removing the supernatant is repeated to remove a cell fusing agent and the like unpreferable for the growth of hybridoma.

In addition to the obtainment of the above-mentioned hybridoma by immunizing an animal other than human with an antigen, a human anti-Embigin antibody producing cell line can also be prepared by sensitizing human lymphocyte, for example, human lymphocyte immortalized by infection with EB virus, with Embigin protein, Embigin protein expressing cell or a lysate thereof in vitro. Furthermore, to stably maintain an antibody secretion ability, a sensitized lymphocyte may be fused with a mouse myeloma cell like the one mentioned above, or a myeloma cell derived from human, which has permanent division potential, for example, U266, to give a hybridoma that produces a human antibody having a desired activity (Embigin binding activity).

The thus-obtained hybridoma is determined by cultivating in a conventional selection culture medium, for example, HAT culture medium (culture medium containing hypoxanthine, aminopterine and thymidine). The culture in the above-mentioned HAT culture medium is continued for a time sufficient to kill cells other than the object hybridoma (unfused cells) (generally several days-several weeks). Then, a conventional limiting dilution method is performed, and screening and single cloning of a hybridoma that produces the object antibody are performed.

The thus-prepared hybridoma that produces a monoclonal antibody can be passage-cultivated in a conventional culture medium, and can be preserved for a long term in liquid nitrogen. To obtain a monoclonal antibody from the hybridoma, a method including cultivating the hybridoma according to a conventional method to give the antibody in the culture supernatant thereof, or a method including administering hybridoma to a mammal compatible therewith and obtaining the proliferated cells in ascites fluid or the like is adopted. The former method is suitable for obtaining a highly pure antibody and the latter method is suitable for a large-scale production of an antibody.

The human antibody means an antibody as an expression product of a human-derived antibody gene. The human antibody can be obtained by, for example, introducing a human antibody gene locus into a transgenic animal to impart an ability to produce a human-derived antibody and administering an antigen to the animal. As such transgenic animal, mouse can be mentioned, and a production method of a mouse capable of producing a human antibody is described in, for example, WO02/43478.

The monoclonal antibody in the present invention encompasses a monoclonal antibody consisting of a heavy chain and/or a light chain having each amino acid sequence of the heavy chain and/or the light chain constituting the antibody, wherein one to several amino acids are deleted, substituted or added. Such partial alternation (deletion, substitution, insertion, addition) of amino acids into the amino acid sequence of the antibody of the present invention can be introduced by partially altering the base sequence encoding the amino acid sequence. Such partial alteration of the base sequence can be introduced using a known site specific mutagenesis according to a conventional method (Proc. Natl. Acsd. Sci. USA., 1984 Vol. 81, 5662-5666; Sambrook et al., Molecular Cloning A Laboratory Manual (1989) Second edition, Cold Spring Harbor Laboratory Press).

In the present invention, a gene recombinant antibody artificially altered in an attempt to decrease heterologous antigenicity to human and the like, for example, chimeric (type) antibody and humanized antibody, can also be used. These altered antibodies can be produced using a known method.

The chimeric antibody is an immunoglobulin molecule characterized by the binding of two or more parts derived from different animal species. Generally, a variable region of chimeric antibody is derived from an antibody of a mammal other than human (e.g., mouse monoclonal antibody), and the immunoglobulin constant region thereof derives from a human immunoglobulin molecule. Preferably, a variable region having low immunogenicity is selected and combined with a human constant region also having low immunogenicity. Preferably, the combination also has low immunogenicity. The chimerice antibody contains monovalent, divalent or polyvalent immunoglobulin. The monovalent chimeric antibody is a dimer (HL) formed by a chimeric H chain bound to a chimeric L chain via disulfide bridge. The divalent chimeric antibody is a tetramer (H2L2) formed by two HL dimmers bound via at least one disulfide bridge.

The chimeric antibody and a production method thereof are already described in the technical field (Morrison et al., Proc. Natl. Acad. Sci. USA 81: 6851-6855 (1984); Boulianne et al., Nature 312: 643-646 (1984); Liu et al., Proc. Natl. Acad. Sci. USA 84: 3439-3443 (1987); Sun et al., Proc. Natl. Acad. Sci. USA, 84: 214-218 (1987); Better et al., Science 240: 1041-1043 (1988); and Harlow and Lane, ANTIBODIES: A LABORATORY MANUAL Cold Spring Harbor Laboratory (1988)).

A humanized antibody is also referred to as a reshaped human antibody, which is obtained by transplanting a complementarity determining region (CDR) of an antibody of a mammal other than human, for example, mouse, into a complementarity determining region of human antibody, and a general gene recombination method therefor is also known (see EP-A-EP125023 and WO92/19759). A humanized antibody can be produced by a known method. For example, a DNA sequence designed to link CDR of mouse antibody and a framework region of human antibody (FR; framework region) is synthesized by a PCR method from several oligonucleotides prepared to have an overlapping region on the terminal. The obtained DNA is linked to DNA encoding human antibody C region and then incorporated into an expression vector, which is introduced into a host to allow production, whereby a humanized antibody is obtained (see EP-A-EP239400 and WO92/19759). As the framework region of human antibody, which is linked via CDR, one wherein a complementarity determining region forms a good antigen binding site is selected. Where necessary, amino acid in the framework region of a variable region of the antibody may be substituted such that the complementarity determining region of the reshaped human antibody forms an appropriate antigen binding site (Sato, K. et al., Cancer Res. (1993) 53, 851-856).

For the chimeric antibody and humanized antibody, a human antibody C region is used. As the human antibody C region, Cγ can be mentioned and, for example, Cγ1, Cγ2, Cγ3 or Cγ4 can be used. In addition, to improve the stability of an antibody or production thereof, human antibody C region may be modified. Chimeric antibody consists of a variable region of an antibody derived from a mammal other than human and human antibody-derived C region, and the humanized antibody consists of a complementarity determining region of an antibody derived from a mammal other than human, and human antibody-derived framework region and C region. Since the antigenicity in the human body is low, it is useful as an antibody to be used in the present invention.

The antibody to be used in the present invention may be a fragment of an antibody or a modified form thereof as long as it can be preferably used for the present invention. Examples of the fragment of antibody include Fab, F(ab')2, Fv or single strand antibody (scFv) wherein H chain (VH) and L chain (VL) of Fv are linked to form Fv with a suitable linker, diabody wherein a dimer of polypeptide containing VH and VL are assembled by intermolecular VH-VL interaction, minibody which is a dimmer wherein a part of a constant region ($CH_3$) is bound to H chain of scFv, other small antibodies and the like.

The small antibody is not particularly limited as long as it contains an antibody fragment deficient in a part of the full-length antibody (whole antibody, e.g., whole IgG etc.), and has a binding potential to an antigen (Embigin protein). The antibody fragment is not particularly limited as long as it is a part of the full-length antibody, and preferably contains a heavy chain variable region (VH) or/and light chain variable region (VL).

The single strand antibody is also referred to as "single chain Fv", that is, "scFv" antibody fragment, and contains a VH and VL domains of an antibody, and these domains exist in a polypeptide single chain. The "Fv" fragment is a smallest antibody fragment and contains a complete antigen recognition site and a binding site. Generally, the "Fv" fragment is a dimer (VH-VL dimer) wherein one VH and VL are strongly liked by a noncovalent bond. Three complementarity determining regions (CDR) of each variable region interact to form an antigen binding site on the surface of the VH-VL dimer. Six CDRs form an antigen binding site of an antibody. Even one variable region (or a half of Fv containing only three CDRs specific to antigen) has an ability to recognize and bind to an antigen, though the affinity is lower than that of the whole binding site. The scFv polypeptide further contains a polypeptide linker between VH and VL domains so that scFv can form a desired structure for antibody binding (Pluckthun, The Pharmacology of Monoclonal Antibodies, vol. 113, Rosenburg and Moore eds. Springer-Verlag, New York, pp. 269-315 (1994)).

A small antibody and a single strand antibody can be produced by, for example, treating an antibody with an enzyme (e.g., papain and pepsin) to produce antibody fragments, or constructing a gene encoding these antibody fragments and introducing the same into an expression vector to allow expression in a suitable host cell (see, for example, Co, M. S. et al., J. Immunol. (1994) 152, 2968-2976, Better, M. & Horwitz, A. H. Methods in Enzymology (1989) 178, 476-496, Pluckthun, A. & Skerra, A. Methods in Enzymology (1989) 178, 497-515, Lamoyi, E., Methods in Enzymology (1989) 121, 652-663, Rousseaux, J. et al., Methods in Enzymology (1989) 121, 663-669, Bird, R. E. et al., TIBTECH (1991) 9, 132-137).

scFv can be obtained by linking an H chain V region and L chain V region of an antibody. These regions exist in a single polypeptide chain. Generally, Fv polypeptide further contains a polypeptide linker between VH and VL, whereby scFv can form a structure necessary for antigen binding (see Pluckthun "The Pharmacology of Monoclonal Antibodies" Vol. 113 (Rosenburg and Moore ed (Springer-Verlag, New York) pp. 269-315, 1994) for review of scFv). The linker is not particularly limited as long as it does not inhibit expression of an antibody variable region linked to the both ends thereof.

In this scFv, the H chain V region and L chain V region are linked via a linker, preferably, a peptide linker (Huston, J. S. et al., Proc. Natl. Acad. Sci. U.S.A. (1988) 85, 5879-5883). The H chain V region and L chain V region in scFv may be derived from any of those described above as antibodies. As the peptide linker that links V regions, for example, an optional single strand peptide consisting of 12-19 amino acid residues is used.

DNA encoding scFv is obtained by using a DNA encoding H chain or H chain V region of the aforementioned antibody, and a DNA encoding L chain or L chain V region thereof as templates, amplifying a DNA part encoding the desired amino acid sequence of those sequences by PCR method using primer sets defining the both ends, and then amplifying, in combination, a DNA encoding a peptide linker part and primer sets that define such that the both ends are linked to H chain and L chain, respectively. Once a DNA encoding scFv is prepared, an expression vector containing the same and a host transformed with said expression vector can be obtained according to a conventional method, and scFv can be obtained using the host according to a conventional method.

The diabody means a bivalent antibody fragment constructed by gene fusion (Holliger P et al., Proc. Natl. Acad. Sci. USA 90: 6444-6448 (1993), EP-A-404097, WO93/11161 etc.). The diabody is a dimer constituted with two polypeptide chains. Generally, in the polypeptide chains, VL and VH are respectively linked in the same chain by a short linker having, for example, about 5 residues, which is too short to allow them to bind to each other. VL and VH coded on the same polypeptide chain cannot form a single chain variable region fragment, since the linker between them is short, but form a dimer, and therefore, the diabody has two antigen binding sites.

sc(Fv)2 is a small antibody consisting of two VHs and two VLs linked by a linker and the like into a single strand (Hudson et al., J Immunol. Methods 1999; 231: 177-189). sc(Fv)2 can be prepared by, for example, binding two scFvs by a linker.

In the present invention, as the linker that links a variable region of an antibody, a peptide linker that can be introduced by genetic engineering, a synthetic compound linker (e.g., a linker disclosed in Protein Engineering, 9(3), 299-305, 1996) or the like can be used. When a peptide linker is used, the length thereof is not particularly limited, and those of ordinary skill in the art can appropriately select the length according to the object. The length is generally 1-100 amino acids, preferably 3-50 amino acids, further preferably 5-30 amino acids, particularly preferably 12-18 amino acids (e.g., 15 amino acids). The synthetic compound linker (chemical crosslinking agent) is a crosslinking agent generally used for crosslinking peptides. Examples thereof include N-hydroxysuccinimido (NHS), disuccinimidyl suberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidyl succinate) (EGS), ethyleneglycol bis(sulfosuccinimidyl succinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), bis[2-(sulfosuccinimidooxycarbonyloxy)ethyl]sulfone(sulfo-BSOCOES) and the like. These crosslinking agents are commercially available.

Fragments of these antibodies can be produced by obtaining the gene thereof in the same manner as above, expressing the gene, and allowing production thereof by a host. The "antibody" in the Claims of the present application also encompasses those antibody fragments.

Examples of the modified antibody include antibodies conjugated with various molecules such as polyethylene glycol (PEG), fluorescent substance, radioisotope, drug and the like. The "antibody" in the Claims of the present application also encompasses these modified antibodies. Such modified antibodies can be obtained by applying chemical modification to the obtained antibody. The methods and therefor have already been established in this field.

Examples of the antibody having an enhanced cytotoxicity inducing activity include a fucose-deficient antibody, an antibody added with bisecting N-acetylglucosamine (GlcNAc) at sugar chain, an antibody with altered binding activity to Fcγ receptor by substituting the amino acid in the Fc region and the like. These antibodies with enhanced cytotoxicity inducing activity can be produced by a method known to those of ordinary skill in the art.

When an antibody in a different subclass is converted to human IgG1, it can be obtained by, for example, isolating only a coding region of a variable region from a cDNA derived from antibody producing hybridoma, and introducing same into a vector containing a constant region of human IgG1, for example, N5KG1-Val Lark vector (IDEC Pharmaceuticals, N5KG1 (U.S. Pat. No. 6,001,358)).

The bispecific antibody is an antibody that recognizes two kinds of antigens and a preparation method thereof is also known (e.g., Journal of Immunology, 1994, 152, 5368-5374). One of the antigens is Embigin, and the other is a heterologous antigen other than Embigin. Examples of the heterologous antigen include, but are not limited to, other cell surface antigens of immune effector cells, for example, CD3, CD28, CD16, CD64 and the like.

An antibody fused with a protein is an antibody fused with a heterologous protein at the N-terminus or C-terminus of the antibody, and a preparation method thereof is also known (e.g., Clinical Cancer Research, 2004, 10, 1274-1281). The antibody only needs to be a chimeric molecule obtained by binding a heterologous protein to an anti-Embigin antibody. Examples of the heterologous protein include, but are not limited to, Fc receptor, cytokine and the like.

The antibody produced and expressed as mentioned above can be separated from the inside and outside of cell, and a host, and uniformly purified. The antibody to be used in the present invention can be separated and purified by affinity chromatography. Examples of the column to be used for affinity chromatography include protein A column and protein G column. Examples of the carrier to be used for protein A column include HyperD, POROS, Sepharose F.F. and the like. In addition, separation and purification methods generally used for proteins may be used, and are not limited at all.

For example, the antibody used in the present invention can be separated and purified by appropriately selecting and combining chromatography other than the above-mentioned affinity chromatographys, filtering, ultrafiltration, salting out, dialysis and the like. Examples of the chromatography include ion exchange chromatography, hydrophobic chromatography, gel filtration and the like. These chromatographys can be applied to HPLC (High performance liquid chromatography). In addition, reversed-phase HPLC may also be used.

2. Agent for Prophylaxis or Therapy of the Present Invention and Cytotoxic Agent to Th17 Cell The present inventors have found that, since a toxin-modified anti-Embigin antibody and an anti-Embigin antibody conjugated with magnetic beads selectively deplete Th17 cells, and further, an anti-Embigin antibody, which is rat IgG2b, not only selectively decreases Th17 cells but also shows a prophylactic or therapeutic effect for autoimmune disease model animals, an anti-Embigin antibody, for example, an anti-Embigin antibody conjugated with a drug showing cytotoxicity, an anti-Embigin antibody having a structure to induce cytotoxicity and the like are utilizable as an agent for the prophylaxis or therapy of an autoimmune or allergic disease associated with Th17 cell, particularly an agent for the prophylaxis or therapy of multiple sclerosis.

Therefore, the present invention provides an agent for the prophylaxis or therapy of an autoimmune disease or allergic disease, which contains an anti-Embigin antibody.

The anti-Embigin antibody contained in the agent for the prophylaxis or therapy of autoimmune disease or allergic disease of the present invention is not particularly limited as long as it is an antibody described in "1. anti-Embigin antibody in the present invention". For example, an anti-Embigin antibody showing cytotoxicity, an anti-Embigin antibody having a cytotoxicity inducing activity and the like can be preferably used.

Examples of the "cytotoxicity" include cell-killing activity, cell dysfunctioning activity and cell growth suppressive activity. In the present invention, at least one of these activities needs to be present. In addition, the anti-Embigin antibody itself may have a cytotoxicity (e.g., ADCC.CDC-independent apoptosis induction activity etc.), and preferably, a drug showing cytotoxicity can be used by conjugating same with an antibody to impart a cytotoxicity against the antibody.

Examples of the drug showing cytotoxicity include cytotoxic substances such as bacterium-derived toxin and the like, chemotherapeutic agents and radioisotopes. Specific examples thereof include radionuclides such as iodo ($^{131}$Iodine: $^{131}$I, $^{125}$Iodine: $^{125}$I), yttrium ($^{90}$Yttrium: $^{90}$Y), indium ($^{111}$Indium: $^{111}$In), technetium ($^{99m}$Technetium: $^{99m}$Tc) and the like (J. W. Goding., Monoclonal Antibodies: principles and practice., 1993 ACADEMIC PRESS), bacterium-derived toxin such. as *Pseudomonas aeruginosa* toxin (Pseudomonas exotoxin), diphtheria toxin, and Ricin, chemotherapeutic agents such as Methotrexate, mitomycin, Calicheamicin, saporin and the like (D. J. King., Applications and Engineering of Monoclonal Antibodies., 1998 T.J. International Ltd, M. L. Grossbard., Monoclonal Antibody-Based Therapy of Cancer., 1998 Marcel Dekker Inc, John M Lambert, Current Opinion in Pharmacology (2005) vol. 5, p 543-549) and the like. A drug having no side effects and strong cytotoxicity is preferable.

The bond between an antibody and a drug may be any of a covalent bond and a noncovalent bond (e.g., ion bond). For example, a complex of an anti-Embigin antibody and a drug can be obtained by utilizing a reactive group (e.g., amino group, carboxyl group, hydroxyl group etc.) or a coordinating group in an antibody molecule, and contacting a drug having a functional group capable of forming a bond upon reaction with said reactive group (in the case of bacterium-derived toxin or chemotherapeutic agents) or having an ionizable group capable of forming a complex with the coordinating group (in the case of radionuclide) with an antibody, wherein the reactive group can be utilized after being bounded by or converted to a group having higher reactivity, if necessary. Alternatively, a biotin-avidin system can also be utilized for the formation of the complex. Such binding method has already been established in this field (Bioconjugate Chem. (2010) vol. 21, 5-13, Accounts of chemical research (2008) vol. 41, No. 1, 98-107). Currently, a plurality of IgGs conjugated with a drug showing cytotoxicity have been clinically developed (Current Opinion in Pharmacology (2005) vol. 5, p 543-549). As the anti-Embigin antibody showing cytotoxicity of the present invention, for example, an anti-Embigin antibody, which is IgG, conjugated with a drug showing cytotoxicity can be mentioned.

As the "anti-Embigin antibody having a cytotoxicity inducing activity" in the present specification, an antibody specifically recognizing Embigin and having the aforementioned structure to induce the cytotoxicity can be mentioned. As shown in Examples 14-17, the anti-Embigin antibody having a structure to induce the cytotoxicity selectively eliminates Th17 cells, and shows a prophylactic or therapeutic effect on an autoimmune disease animal model. Therefore, when the anti-Embigin antibody is an antibody having a structure to induce the cytotoxicity, the antibody can exhibit a function as an agent for the prophylaxis or therapy of an autoimmune disease or allergic disease, or a cytotoxic agent to Th17 cell, even when the antibody has no cytotoxicity in itself and is not conjugated with a drug having said activity.

Specific examples of the antibody having a structure to induce the cytotoxicity include the following (a)-(c).

(a) an antibody having a structure to induce an antibody-dependent cellular cytotoxicity (ADCC) in the presence of an effector cell.

(b) an antibody having a structure to induce a complement-dependent cytotoxicity (CDC).

(c) an antibody having a structure to induce an antibody-dependent cellular phagocytosis (ADCP).

The antibody of the above-mentioned (a) having a structure to induce the antibody-dependent cellular cytotoxicity in the presence of an effector cell is widely known. Examples thereof include antibodies belonging to subclasses, such as mouse IgG2a and IgG3, human IgG1 and IgG3, rat IgG2b and the like, and the like.

As a medical antibody of these subclasses, rituximab (trade name Rituxan (Chugai Pharmaceutical Co., Ltd.)), trastuzumab (trade name herceptin (Chugai Pharmaceutical Co., Ltd.)) and the like are known (see, for example, Nat. Rev. Immunol. 2010; 10: 301-316).

The antibody of the above-mentioned (b) having a structure to induce the complement-dependent cytotoxicity is also widely known. Examples thereof include antibodies belonging to subclasses such as mouse IgM, IgG2a and IgG3, human IgM, IgG1 and IgG3, rat IgG2b and the like, and the like.

The ADCC and CDC activities by an antibody greatly depend on the subclass of IgG, and it has been clarified that IgG1 and IgG3 have strong activities in human. Thus, examples of the human antibody having a structure to induce a cytotoxicity include antibodies having a constant region of IgG1, a constant region of IgG3 or a constant region of IgM. Preferable examples of the human antibody having a structure to induce the cytotoxicity include IgG antibody of IgG1 or IgG3 subclass, and IgM antibody.

The cytotoxicity inducing activity of an antibody can be examined by, in the case of ADCC activity, for example, incubating a target cell (Th17 cell and cell line forcibly expressing Embigin) and an effector cell (NK cell, monocyte etc.) expressing Fc receptor in the presence of an anti-Embigin antibody and, in the case of CDC activity, incubating a target cell and an antibody in the presence of a fresh human serum (including complement), and counting viable cells and/or dead cells.

Furthermore, the "anti-Embigin antibody having the cytotoxicity inducing activity" of the present invention also includes an antibody having a structure to induce two kinds of cytotoxic activities, an antibody with enhanced cytotoxicity inducing activity, a bispecific antibody binding to Embigin and an antigen other than Embigin, an anti-Embigin antibody fused with a protein, and the like.

Examples of the antibody with enhanced cytotoxicity inducing activity include an antibody deficient in fucose of Fc region sugar chain, an antibody added with bisecting N-acetylglucosamine (GlcNAc) at the sugar chain, an antibody with altered binding activity to Fcγreceptor by substituting the amino acid in the Fc region and the like. These operations can potentiate the binding activity to Fc receptor on an effector cell to 100 times or more. In addition, when the anti-Embigin antibody belongs to human IgG2 or IgG4 subclass, the constant region can be changed to human IgG1 or IgG3 subclass by the aforementioned gene recombination method. Furthermore, a CDC activity exceeding that of natural subtype IgG1 and IgG3 can be imparted by preparing an isotype chimeric antibody incorporating a part of the human IgG3 sequence into human IgG1 (review in Cancer Res. 2008; 68: 3863-3872; Nat. Rev. Immunol. 2010 (mentioned above)).

The "disease associated with Th17 cell" means a disease wherein Th17 cell is a pathogenic cell, a disease wherein Th17 cell is suspected to be a pathogenic cell, a disease wherein Th17 cell accelerates aggravation of the pathology, or a disease wherein Th17 cell has a possibility of accelerating aggravation of the pathology.

Examples of the disease associated with Th17 cell include autoimmune diseases such as multiple sclerosis, psoriasis, rheumatism, inflammatory bowel disease and the like, allergic diseases such as contact hypersensitivity, steroid-resistant asthma, glomerulonephritis, atopic dermatitis and the like, and chronic obliterative pulmonary disease (COPD). Involvement of Th17 cell in these diseases has already been reported in literature and the like (Annu. Rev. Physiol. (2010) 72: 495-516, J Am Soc Nephrol (2010) 21: 925-931). Particularly, it has been clarified using animal models that Th17 cell is a stronger pathogenic cell in multiple sclerosis than Th1 cell conventionally considered to be important (J. Exp. Med. (2005) 201; 233-240).

In addition, since the main IL-17-producing cell in the body is Th17 cell, diseases associated with IL-17 are also encompassed in the "disease associated with Th17 cell". It is known that diseases such as rheumatoid arthritis, inflammatory bowel disease, psoriasis, chronic noninfectious uveitis and the like can be improved by suppressing IL-17 production or inhibiting the function of IL-17 (J. Immunol. (2003) 171: 6173-6177, Inflamm Bowel Dis (2006): 2: 382-388, Sci Transl Med (2010) 2; 52ra72).

Since both Th1 cell and Th17 cell are also involved in the defensive function of the body, non-specific immunosuppression or inhibition of the function of both Th1 cell and Th17 cell may excessively reduce the defensive function of the body. Therefore, the therapeutic agent of the present invention which selectively acts on the Th17 cell is expected to cause a reduced side effects. In addition, since Th17 cell shows a stronger action as a pathogenic cell of autoimmune diseases than Th1 cell depending on the disease, the therapeutic agent of the present invention shows a superior effect on autoimmune diseases associated with Th17 cell and the like by selectively acting on Th17 cell.

In addition, the present inventors have found that an anti-Embigin antibody conjugated with a drug showing cytotoxicity, or an anti-Embigin antibody having a structure that induces a cytotoxicity is also utilizable as a cytotoxic agent to Th17 cell, since a saporin-modified anti-Embigin antibody and an anti-Embigin antibody conjugated with magnetic beads selectively deplete Th17 cell, and a rat IgG2b antibody, namely, an anti-Embigin antibody which is an antibody capable of inducing ADCC and CDC activities, also selectively deplete Th17 cell.

Accordingly, the present invention provides a cytotoxic agent to Th17 cell, which contains an anti-Embigin antibody.

The "cytotoxic agent to Th17 cell" of the present invention is a drug that causes cellular damage on Th17 cell. Therefore, examples of the cytotoxic agent to Th17 cell of the present invention include the aforementioned anti-Embigin antibody showing cytotoxicity and anti-Embigin antibody having a cytotoxicity inducing activity.

The cytotoxic agent to Th17 cell of the present invention can be used for confirming the involvement of Th17 cell in a certain pathological condition by, for example, administering the agent to various animal disease models.

Heretofore, studies of Th17 cell as a pathogenic cell in autoimmune diseases have been mainly verified by Th17 cell transfer. However, they were not investigations using highly pure Th17 cell for transfer, but those allowing mixing of cell other than Th17 cell (J. Exp. Med. (2005) 233-240). Using the cytotoxic agent to Th17 cell of the present invention, therefore, involvement of Th17 in the pathology can be more clearly analyzed, and the agent of the present invention is useful for the study of therapy of various diseases. For example, as an autoimmune disease model, an experimental autoimmune encephalomyelitis (EAE)-developed model, which is a multiple sclerosis model, can be mentioned, and an EAE model obtained by immunizing peptide (autoantigen) such as PLP or MOG and the like to widely-used mouse and rat can be used (Methods Mol Biol. 2009; 549: 157-73, Brain (2004); 127: 2201-2213), though not limited thereto.

The cytotoxic agent to Th17 cell of the present invention can be further used for the prophylaxis or therapy of the aforementioned "disease associated with Th17 cell".

The effect of the cytotoxic agent to Th17 cell of the present invention can be confirmed by counting the number of Th17 cells according to the method described in the below-mentioned "5. detection method of Th17 cell of the present invention".

The therapeutic agent and the cytotoxic agent to Th17 cell of the present invention can contain an optional carrier, for example, a pharmaceutically acceptable carrier, and can be applied as a drug in the form of a pharmaceutical composition.

Examples of the pharmaceutically acceptable carrier include, but are not limited to, excipients such as sucrose, starch and the like, binders such as cellulose, methylcellulose and the like, disintegrants such as starch, carboxymethylcellulose and the like, lubricants such as magnesium stearate, aerosil and the like, fragrance substances such as citric acid, menthol and the like, preservatives such as sodium benzoate, sodium hydrogen sulfite and the like, stabilizers such as citric acid, sodium citrate and the like, suspensions such as methylcellulose, polyvinylpyrrolidon and the like, dispersing agents such as surfactant and the like, diluents such as water, saline and the like, basewax and the like.

The agent of the present invention can be administered both orally and parenterally, with preference given to parenteral administration. Specific examples thereof include injection dosage form, transnasal administration dosage form, transpulmonary administration dosage form, transdermal administration form and the like. Examples of the injection dosage form include intravenous injection, intramuscular injection, intraperitoneal injection, subcutaneous injection and the like, which can be administered systemically or topically.

While the dose of the agent of the present invention varies depending on the administration objective, administration method, administration route, dosage form, condition of the administration subject (sex, age, body weight, severity etc.), when administered by injection to an adult, the dose can be generally determined to fall within the range of 0.0001 mg-100 mg per 1 kg body weight or 1-1000 mg, preferably 5-50 mg, per patient per single. injection. However, the agent and/or composition of the present invention are/is not limited to these doses.

In addition, as for the administration interval, the next administration may not be given as long as the effect continues. For example, the administration may be necessary once every 2-8 weeks, once every several weeks or several months, or once every several years, during the treatment.

The agent of the present invention is formulated according to a known pharmaceutical method and administered. For example, it can be used in the form of an injection of a sterile solution or suspension in water or other pharmaceutically acceptable liquid. In addition, it may be formulated by appropriately combining with, for example, a pharmacologically acceptable carrier or medium, specifically, sterile water and saline, emulsifier, suspending agent, surfactant, stabilizer, vehicle, preservative and the like, and admixing in the unit dosage form required for generally-admitted pharmaceutical application. The amount of the active ingredient in these preparations should be set to be a suitable volume within the indicated range.

The sterile composition for injection can be formulated according to a general preparation application and using a vehicle such as distilled water for injection. Examples of the aqueous solution for injection include saline, isotonic solutions including glucose and other auxiliary agents, such as D-sorbitol, D-mannose, D-mannitol, and sodium chloride, and they may be used in combination with a suitable dissolution aid (e.g., alcohol, specifically ethanol), polyalcohol (e.g., propylene glycol, polyethylene glycol), and non-ionic surfactant (e.g., polysorbate 80™, HCO-50).

Examples of the oily liquid include sesame oil and soybean oil, and they may be used in combination with benzyl benzoate and benzyl alcohol as a dissolution aid. In addition, buffer (e.g., phosphate buffer, sodium acetate buffer), soothing agent (e.g., procaine hydrochloride), stabilizer (e.g., benzylalcohol, phenol), and antioxidant may be used in combination. A prepared injection solution is generally filled in a suitable ampoule.

3. Anti-Embigin Antibody for Drug Delivery System of the Present Invention

The present invention provides a drug delivery system (DDS) for delivering a drug to Th17 cell and an anti-Embigin antibody useful for the DDS.

The present inventors have found that, since Embigin is highly expressed in Th17 cell as compared to other blood cells, and toxin-modified anti-Embigin antibody and anti-Embigin antibody conjugated with magnetic beads deplete Th17 cell, an anti-Embigin antibody is utilizable for a drug delivery system that delivers a drug to Th17 cell.

Since an anti-Embigin antibody for the drug delivery system of the present invention specifically binds to Embigin, which is a cellular membrane surface antigen of Th17 cell, a complex formed by conjugating an objective drug with said antibody can deliver the drug to Th17 cell.

Examples of the anti-Embigin antibody include antibodies described in detail in "1. anti-Embigin antibody in the present invention". It may also be a commercially available anti-Embigin antibody (e.g., anti-Embigin antibody sold by Santa Cruz etc.).

The drug is not particularly limited as long as it can form a complex with the anti-Embigin antibody. Examples thereof include cytotoxic substances such as bacterium-derived toxin and the like, chemotherapeutic agent and radioisotope. Specific examples thereof include the drugs described in detail in "2. Therapeutic agent and cytotoxic agent to Th17 cell of the present invention". Preferred as the drug is one free of side effects, and showing strong cytotoxicity such as cell-killing activity, cell growth suppressive activity and the like. A binding method of a drug and an antibody has already been established in this field.

The drug delivery system (DDS) of the present invention is a drug delivery system characterized by administration of a complex of an anti-Embigin antibody and a drug, and can deliver the objective drug to Th17 cell.

The DDS of the present invention can be applied in vitro and in vivo.

In the case of "in vitro", a drug can be delivered to Th17 cell by adding a complex of an anti-Embigin antibody and the drug to a medium for cultivating cultured cells or cells collected from a mammal.

In the case of "in vivo", a drug can be delivered to Th17 cell in the body by subcutaneous administration, intravenous administration, administration by an osmotic pump, administration via tail vein and the like of a complex of an anti-Embigin antibody and the drug to an individual mammal. Examples of the mammal include human, monkey, mouse, rat and the like.

4. Th17 Cell Detection Reagent and Kit of the Present Invention

While Th17 cell is known to associate with various diseases, a Th17 cell-specific cell surface molecule has not been reported yet.

The present inventors have found that Embigin or Embigin gene is utilizable as a Th17 cell marker, since Embigin is highly expressed in mouse Th17 cell and human Th17 cell and, particularly among blood cells, Th17 cell highly expresses Embigin as compared to other blood cells.

The Th17 cell detection reagent of the present invention contains an anti-Embigin antibody or a nucleic acid capable of specifically detecting Embigin gene transcription product.

Examples of the anti-Embigin antibody include the antibodies described in detail in "1. anti-Embigin antibody of the present invention". In addition, the anti-Embigin antibody may be a modified antibody labeled with a fluorescent substance or radioisotope. As the label, one similar to that in the below-mentioned nucleic acid can be used. Examples of the fluorescent substance include fluorescamine, fluorescein isothiocyanate and the like, and examples of the radioisotope include $^{125}$I, $^{131}$I, $^{3}$H, $^{14}$C and the like. Labeling of the antibody with a fluorescent substance or radioisotope can be performed according to a conventional method. Using an anti-Embigin antibody labeled with a fluorescent label and the like, Th17 cell can be easily detected by FACS and the like.

The "nucleic acid capable of specifically detecting an Embigin gene transcription product" may be any nucleic acid as long as it can specifically detect mRNA of Embigin, and a probe or primer can be appropriately selected and used according to the detection method. Examples of the probe include a polynucleotide sequence comprising a continuous nucleotide sequence of 15 bases or more, preferably 18 bases or more, more preferably about 20 bases or more, most preferably full-length, of the nucleic acid sequence of Embigin mRNA, or a complementarily sequence thereof. Examples of the primer include a polynucleotide sequence comprising a pair of DNA sequences consisting of 15 bases or more, preferably 18 bases or more, more preferably about 20 bases or more and 100 bases or less, preferably 50 bases or less, more preferably about 40 bases or less, which provide a PCR-amplified sequence having a length of, for example, 100 bases or more, preferably 200 bases or more and, for example, 1000 bases or less, preferably 500 bases or less, and which are respectively contained in the nucleic acid sequence of Embigin mRNA and a complementally strand sequence thereof.

The nucleic acid probe or primer may contain an additional sequence (nucleotide sequence noncomplementary to the detection subject polynucleotide) as long as the specific detection is not impaired.

In addition, the nucleic acid probe and primer may also be labeled with a suitable label, for example, radioisotope (e.g., $^{125}$I, $^{131}$I, $^{3}$H, $^{14}$C etc.), enzyme (e.g., β-galactosidase, β-glucosidase, alkaline phosphatase, peroxidase, malic acid dehydrogenase etc.), fluorescent substance (e.g., fluorescamine, fluorescein isothiocyanate etc.), luminescent substance (e.g., luminol, luminol derivative, luciferin, lucigenin etc.) and the like. Alternatively, a quencher (quenching substance) that absorbs fluorescence energy emitted by a fluorescent substance (e.g., FAM, VIC etc.) may be further conjugated near the fluorescent substance. In such embodiment, fluorescence is detected when the fluorescent substance and quencher are separated during the detection reaction.

The nucleic acid probe may be any of DNA, RNA and chimeric nucleic acid, and a single strand or double strand. Based on known information relating to the nucleic acid sequence of Embigin gene (e.g., nucleic acid sequence of human Embigin gene shown by SEQ ID NO: 2), the nucleic acid probe capable of specifically detecting an Embigin gene transcription product can be synthesized according to a conventional method and using, for example, a DNA/RNA automatic synthesizer.

The present invention also provides a kit for detecting Th17 cell. The kit for Th17 cell detection of the present invention contains a reagent for measuring the expression of Embigin. Th17 cell can be conveniently detected by measuring the expression of Embigin using the kit of the present invention.

The kit of the present invention contains an anti-Embigin antibody or a nucleic acid capable of specifically detecting Embigin gene transcription product, specifically the aforementioned reagent for Th17 cell detection.

The anti-Embigin antibody or nucleic acid contained in the reagent for Th17 cell detection is generally contained in the kit of the present invention in the form of an aqueous solution thereof dissolved in water or a suitable buffer (e.g., TE buffer, PBS etc.) at a suitable concentration, or in the form of a nucleic acid array wherein the nucleic acid probe is immobilized on a solid phase carrier.

The kit of the present invention may further contain, in its constitution, other components necessary for performing the method, according to the measurement method of Embigin. For example, when Northern blotting or nucleic acid array is used for the measurement, the kit of the present invention can further contain a blotting buffer, a labeling reagent, a blotting membrane and the like. The kit of the present invention may further contain labeling reagent, chromogenic substrate and the like when using in situ hybridization for the measurement. In addition, the kit can contain fluorescent labeled secondary antibody, cell fixative and the like when using FACS for the measurement.

5. Th17 Cell Detection Method of the Present Invention

The present inventors have found that Embigin is highly expressed in mouse Th17 cell and human Th17 cell and, particularly in blood cells, Embigin is highly expressed in Th17 cell as compared to other blood cells, based on which they have found a detection method of Th17 cell using expression of Embigin as an index.

The Th17 cell detection method of the present invention contains a step of measuring the expression of Embigin in a cell or tissue, and a step of detecting Th17 cell based on the positive correlation between the expression level and Th17 cell. According to the present invention, Th17 cell can be detected more easily than before.

The "expression of Embigin" in the present invention means the expression of an Embigin protein or Embigin gene.

The method of the present invention can be concretely performed by measuring the expression of Embigin in a cell or tissue. The cell only needs to be a cell obtained from a test animal or a cultured cell, and an obtained blood cell or a cultured cell derived from a blood cell is preferable. The tissue only needs to be a tissue obtained from a test animal, and it is preferably in a form permitting immunostaining.

The method of the present invention can be applied to, for example, a cell, a tissue and the like obtained from a test animal such as human, rat, mouse and the like.

The expression of Embigin can be measured using the aforementioned reagent for Th17 cell detection of the present invention and according to a method known per se. Examples of the measurement method include FACS, Western blotting, RT-PCR, Northern blotting, in situ hybridization, nucleic acid array, tissue staining and the like.

Then, based on the measured expression level of Embigin, Th17 cell can be detected. As shown in the below-mentioned Examples, since the expression level of Embigin is high in Th17 cell, a cell can be judged to be Th17 cell when the expression level or concentration of Embigin is high in a cell or tissue of a measurement subject, based on the positive correlation between the Embigin expression level and Th17 cell.

Heretofore, a cell surface molecule of Th17 cell that enables identification of Th17 cell by using a single molecule has not been found. However, the Th17 cell detection method of the present invention can detect Th17 cell using a convenient method such as FACS and the like. Particularly, when the method of the present invention is applied to a blood cell or blood-derived cultured cell, Th17 cell can be easily detected. Therefore, the method of the present invention is extremely useful for the study of autoimmune diseases and allergic diseases involving Th17 cell, inspection of the presence or absence of an increase of Th17 cell in a test animal, and the like.

EXAMPLES

The present invention is explained in the following by referring to Examples, which are not to be construed as limitative.

Reference Example 1-1

Preparation of Antibody to Mouse Embigin (1)

A retrovirus for expression of mouse Embigin was introduced into rat cell to prepare a mouse Embigin overexpressing cell. Rat (Wistar, 5-week-old, CLEA Japan, Inc.) was immunized with the mouse Embigin overexpressing cell. After immunization, lymphocytes were obtained and fused with myeloma cells by the PEG method to give hybridomas.

An anti-mouse Embigin antibody-producing hybridoma was screened for by flow cytometry using, as a positive control cell, the mouse Embigin overexpressing cell used for the immunization and, as a negative control cell, the same host cell as for the positive control cell, into which a vector alone was introduced.

The binding activity was evaluated by flow cytometry as follows.

The positive control cells or negative control cells were used at $1\times10^4$–$1\times10^6$ cells, hybridoma culture supernatant or suitable rat IgG was added at 5 μg/mL, and the mixture was reacted for 30 min. The cells were washed once with FACS buffer, a fluorescent labeled anti-rat IgG antibody was added, and the mixture was reacted for 30 min. After the reaction, the cells were collected by a centrifugal operation, suspended in PBS or FACS buffer, and subjected to flow cytometry. The flow cytometer used was flow cytometer FC500 (Beckman Coulter). A gate was set on a living cell population using forward scatter and side scatter histograms, and analysis was performed.

Hybridomas (2G21, 2G23, 3E64, 3E66) strongly reactive only with positive control cells expressing Embigin were obtained. FIG. 1 shows the evaluation results.

Figure 2:
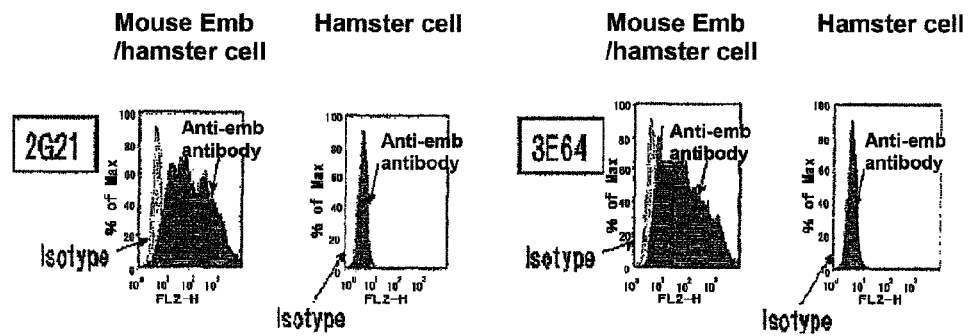
FIG. 2 is a figure showing evaluation of a binding activity of an anti-Embigin antibody to mouse Embigin expressing hamster cells and hamster cells by flow cytometry. Isotype was 5 μg/mL concentration, and a culture supernatant was used as the anti-Embigin antibody (anti-emb antibody).

To further confirm reaction specificity, 2G21 and 3E64 were evaluated by flow cytometry using cells overexpressing mouse Embigin (host: hamster cell) as a positive control cell and hamster cells introduced only with a vector as a negative control cell. The analysis was performed using flow cytometer FACS Calibur (Becton, Dickinson and Company), and strong reaction of both 2G21 and 3E64 only with the positive control cell was confirmed. FIG. 2 shows the evaluation results.

Reference Example 1-2

Preparation of Antibody to Mouse Embigin (2)

The anti-Embigin antibody 3E64 prepared in the above-mentioned Reference Example 1-1 was further subjected to single cloning by a limiting dilution method using a 96-well plate. The antibody of this clone was purified to give an anti-Embigin antibody (3E64D1).

In addition, this antibody clone was confirmed to be a rat IgG2b antibody. The rat IgG2b is known to have a structure that induces a cytotoxicity.

Reference Example 2

Preparation of Mouse Various Helper T Cells (1) Preparation of Mouse Th17 Cell

Mouse Th17 cells were prepared by reference to published references (Nature Immunology (2007) Vol. 8 903-905, Nature is Immunology (2007) Vol. 8 958-966, Nature Immunology (2007) Vol. 8 1390-1397, Nature (2007) Vol. 448 480-484, J. Biol. Chem. (2008) Vol. 283 17003-17008).

The spleen was isolated from SJL mouse (CHARLES RIVER LABORATORIES JAPAN, INC.) or Rag2 KO/DO11.10 Tg mouse (Taconic Farms, Inc.), and a cell suspension was prepared. The cell suspension was filtered with a cell strainer (diameter 70 µm, Becton, Dickinson and Company) and centrifuged (300×g, 4° C., 5 min), and the supernatant was removed. After hemolysis with an ACK solution (TAKARA BIO INC.), the cells were washed with RPMI1640 (Nacalai Tesque) to prepare splenocytes. When prepared from SJL mouse, $CD4^+T$ cells were prepared from the washed cells using a $CD4^+$ T cell isolation kit (Miltenyi Biotec K.K.).

$CD4^+T$ cells were cultured on an anti-CD3ε/anti-CD28 antibody solid-phased plate. For culture, a 10% fetal bovine serum-containing IMDM medium (Invitrogen) added with 20 ng/mL Mouse IL-6, 3 ng/mL Mouse TGF-β1, 20 ng/mL Mouse IL-23, 10 µg/mL Anti-Mouse IFN-γ antibody, 10 µg/mL Anti-mouse IL-4 antibody and 10 µg/mL Anti-mouse IL-2 antibody was used, and the cells were appropriately maintained by subculture and induced to differentiate into Th17 cells. The Th17 cells subjected to differentiation induction for 5-14 days were used for the test.

(2) Preparation of Mouse Treg Cell $CD4^+T$ cells were prepared from mouse spleen and cultured on an anti-CD3ε/anti-CD28 antibody solid-phased plate. For culture, a 10% fetal bovine serum-containing RPMI1640 medium added with 20 ng/mL Mouse TGF-β1, 100 IU/mL Mouse IL-2, 100 nM retinoic acid (all-trans) and 10 µg/mL Anti-Mouse IL-6 was used, and the cells were appropriately maintained by subculture and induced to differentiate into Treg cells. The Treg cells after differentiation induction for 5-14 days were used for the test.

(3) Preparation of Mouse Th1 Cell $CD4^+T$ cells were prepared from mouse spleen and cultured on an anti-CD3ε/anti-CD28 antibody solid-phased plate. For culture, a 10% fetal bovine serum-containing RPMI1640 medium added with 20 ng/mL Mouse IL-12 and 10 µg/mL Anti-mouse IL-4 was used, and the cells were appropriately maintained by subculture and induced to differentiate into Th1 cells. The Th1 cells after differentiation induction for 5-14 days were used for the test.

(4) Preparation of Mouse Th2 Cell $CD4^+T$ cells were prepared from mouse spleen and cultured on an anti-CD3ε antibody/anti-CD28 antibody solid-phased plate. For culture, a 10% fetal bovine serum-containing RPMI1640 medium added with 20 ng/mL Mouse IL-4, 5 µg/mL Anti-Mouse IFN-γ and 5 µg/mL Anti-Mouse IL-12 was used, and the cells were appropriately maintained by subculture and induced to differentiation into Th2 cells. The Th2 cells after differentiation induction for 5-14 days were used for the test.

(5) Preparation of Mouse Th0 Cell

As for mouse Th0 cell, $CD4^+T$ cells were prepared from mouse spleen and cultured on an anti-CD3ε/anti-CD28 antibody solid-phased plate. For culture, a 10% fetal bovine serum-containing RPMI1640 medium added with 10 µg/mL Anti-Mouse IL-4, µg/mL Anti-Mouse IFN-γ and 10 µg/mL Anti-Mouse IL-12 was used, and the cells were appropriately maintained by subculture to prepare Th0 cells, which were used for the test.

Reference Example 3

Preparation of Antibody to Human Embigin

A human Embigin expressing retrovirus was introduced into mouse cell to prepare a human Embigin overexpressing cell. Mouse (Balb/c, 5-week-old, CLEA Japan, Inc.) was immunized with the human Embigin overexpressing cell. After immunization, lymphocytes were obtained and fused with myeloma cells by the PEG method to give hybridomas.

Figure 6:
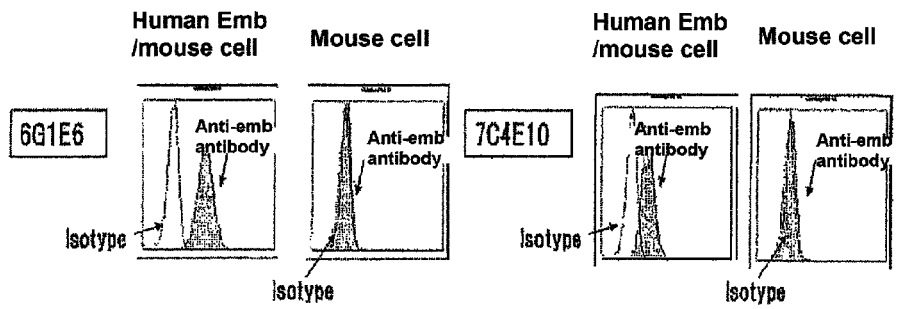
FIG. 6 is a figure showing evaluation of a binding activity of an anti-human Embigin antibody to a mouse cell expressing human gene corresponding to mouse Embigin (*Homo sapiens* Embigin, hereinafter referred to as "human Embigin") and a mouse cell by flow cytometry. Isotype (rat IgG) relative to the anti-human Embigin antibody was 5 μg/mL concentration, and a culture supernatant was used as the anti-Embigin antibody (anti-emb antibody).

An anti-human Embigin antibody-producing hybridoma was screened for by flow cytometry using, as a positive control cell, the human Embigin overexpressing cell used for the immunization and, as a negative control cell, the same host cell as for the positive control cell, into which a vector alone was introduced. Using the flow cytometer FC500 (Beckman Coulter), hybridomas (6G1E6 and 7C4E10) that showed a hybridoma positive reaction strongly reactive only with a positive control cell that expresses Embigin were obtained. FIG. 6 shows the evaluation results.

Reference Example 4

Preparation of Human Th17 Cell

Human Th17 cell was prepared according to a published reference PNAS (2007); 104: 17034-17039.

The memory CD4+T cell and monocyte prepared from human peripheral blood were cultured in a medium containing lipopolysaccharide, anti-CD3ε antibody, anti-IFN-γ antibody, anti-IL-4 antibody and anti-IL-12 antibody for 3 days, further cultured in a medium containing anti-CD2 antibody/anti-CD3 antibody/anti-CD28 antibody solid-phased beads (Cell Activation/Expansion Kit human, Miltenyi Biotec K.K.), IL-2, IL-1β, IL-6, IL-23, anti-IFN-γ antibody, anti-IL-4 antibody and anti-IL-12 antibody for 3-20 days to cause differentiation into Th17 cells.

Example 1

Evaluation of Expression Specificity in Th17 Cell by Western Blotting

To confirm expression specificity in Th17 cell, the Embigin expression levels of Treg cell, which is one of helper T cells, and Th17 cell were compared by Western blotting.

Th17 cell and Treg cell prepared by differentiation from Rag2 KO/DO11.10 Tg mouse or SJL mouse splenocyte were dissolved in a solubilizing buffer containing 80 mM NaCl, 50 mM Tris-HCl (pH 8), 2 mM $CaCl_2$, 1% Triton X-100 and a proteolytic enzyme inhibitor (Complete™, Boehringer Ingelheim), and centrifuged (12000 rpm, 4° C., 30 min). The supernatant was used as a protein solution. The protein solution was mixed with a sample buffer (for SDS-PAGE, 2-fold concentrated, containing 2-mercaptoethanol) (Nacalai Tesque), and an equivalent amount of protein was electrophoresed on 10% SDS-polyacrylamide gel. After electrophoresis, it was transferred to Immobilon-P (Millipore) by using Trans-Blot SD Semi-Dry Electrophoretic Transfer Cell (BIO-RAD). Using the transferred membrane, Western blotting was performed. For the detection, rabbit anti-Embigin polyclonal antibody (IMGENEX) and HRP-labeled goat anti-rabbit Ig antibody (BIOSOURCE) were used. The detection was performed using ECL Plus Western Blotting Detection System (GE Healthcare Japan) by LAS-3000 (Fujifilm).

Figure 3:
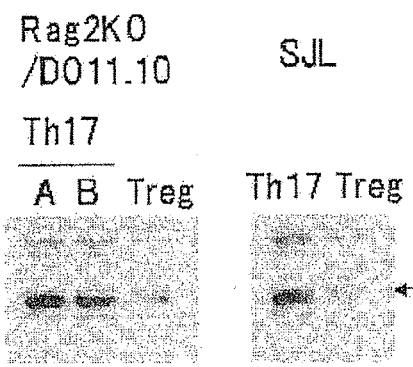
FIG. 3 is a figure showing evaluation of an Embigin amount contained in proteins prepared from Th17 cell and Treg cell by Western blotting.

The results are shown in FIG. 3. It was found that Embigin was scarcely expressed in Treg cell but highly expressed in Th17 cell.

Example 2

Evaluation of Expression Specificity in Helper T Cell by qRT-PCR Method

Total RNAs were prepared from Th17 cell, Th1 cell, Th2 cell, Th0 cell and Treg cell prepared by differentiation from Rag2 KO/DO11.10Tg mouse splenocyte and using TRIzol (Invitrogen). The Embigin mRNA amount in the total RNA was evaluated by TaqMan Reverse Transcription Reagents (Applied Biosystems) and Power SYBR Green PCR Master Mix (Applied Biosystems). The measurement was performed by ABI7900 (Applied Biosystems), and the expression of housekeeping gene 36B4 was simultaneously evaluated. After amendment based on 36B4 expression amount, calculation was made with the expression level of Treg cell as 1.

The detection was performed using Embigin primers (SEQ ID NO: 3 and SEQ ID NO: 4) and 36B4 primers (SEQ ID NO: 5 and SEQ ID NO: 6).

Figure 4:
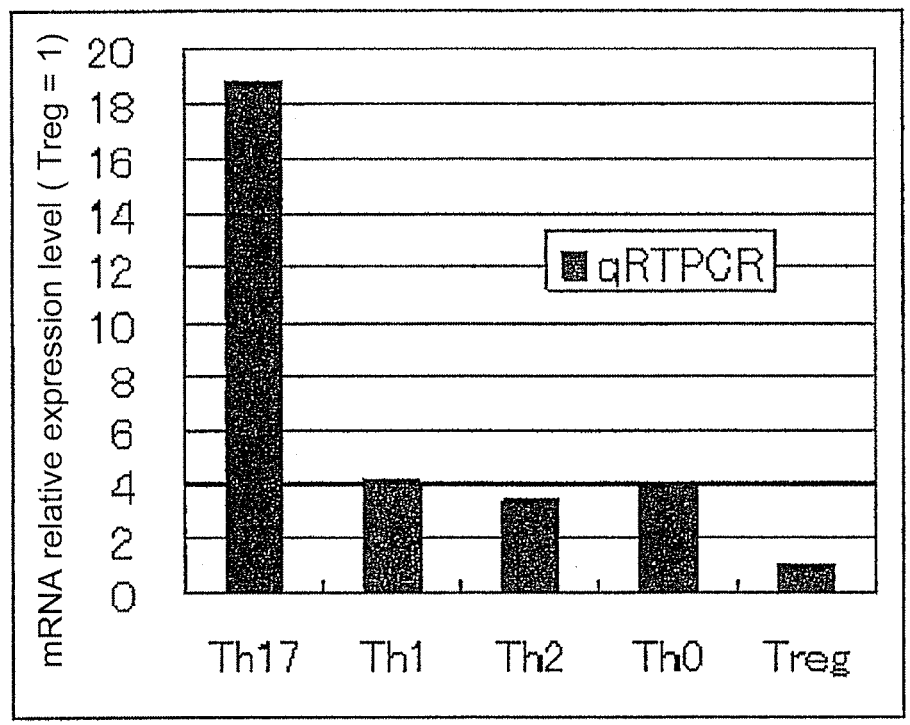
FIG. 4 is a figure showing evaluation of an Embigin mRNA amount contained in total RNA prepared from Th17 cell, Th1 cell, Th2 cell, Th0 cell and Treg cell by a qRT-PCR method.

The results are shown in FIG. 4. Of the mouse helper T cells, Embigin was found to be useful as a marker of Th17 cell, since it was particularly highly expressed in Th17 cell.

Example 3

Evaluation of Th17 Cell Specificity of Cellular Membrane Surface Protein by Flow Cytometry To evaluate expression specificity of cellular membrane surface protein in Th17 cell, comparison with various cells in the expression level was performed by flow cytometry.

Th17 cell, Treg cell, Th1 cell and Th2 cell were differentiated from SJL mouse splenocyte, prepared and subjected to the test. In addition, splenocyte free of differentiation induction and red blood cells prepared from mouse peripheral blood were also subjected to the test.

Embigin was stained with culture supernatants of anti-mouse Embigin antibody-producing clones 2G23, 3E64 and, as secondary antibody, fluorescent labeled goat anti-rat IgM and IgG antibody (Beckman Coulter, Inc.). As a negative control of anti-mouse Embigin antibody, the cells were stained with rat IgG (Becton, Dickinson and Company) in the same manner as in Reference Example 1. As for mouse splenocyte, to identify B cell, leukocyte and CD3 positive cell, they were stained with fluorescent labeled anti-mouse B220 antibody (B cell marker), fluorescent labeled anti-mouse CD11a antibody (leukocyte marker) or fluorescent labeled anti-mouse CD3 antibody (CD3 positive cell marker). These samples were evaluated by flow cytometry. The flow cytometer used was FACS Calibur (Becton, Dickinson and Company). A gate was set on a living cell population using forward scatter and side scatter histograms, and analysis was performed. In analyzing each B cell, leukocyte, CD3 positive cell, each gate in B220, CD11a and CD3 positive fractions was further set, and analysis was performed. Respective samples were compared by the ratio of geo mean value of anti-mouse Embigin antibody to the geo mean value of Isotype (rat IgG).

Figure 5:
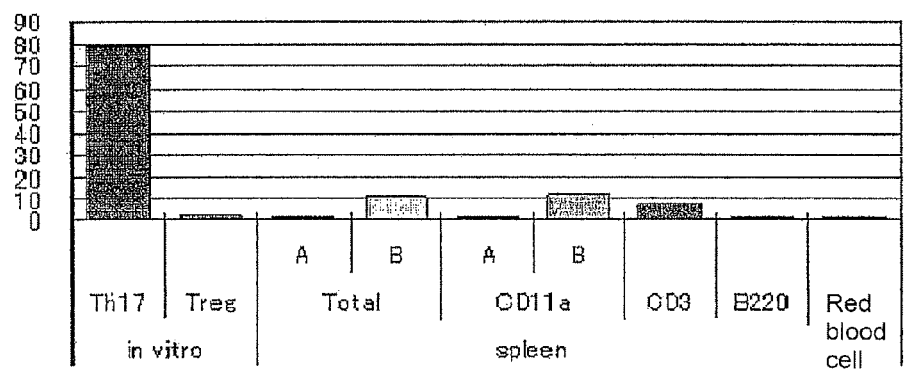
FIG. 5 is a figure showing evaluation of an Embigin amount on a cellular membrane in various cells containing Th17 by flow cytometry. The ratio of geo mean value when using an anti-Embigin antibody relative to geo mean value of Isotype (rat IgG) is shown. When plural peaks were found, each value was shown. Each cell was identified by anti-mouse B220 antibody (B cell marker), anti-mouse CD11a antibody (leukocyte marker) or anti-mouse CD3 antibody (CD3 positive cell marker).
Figure 5:
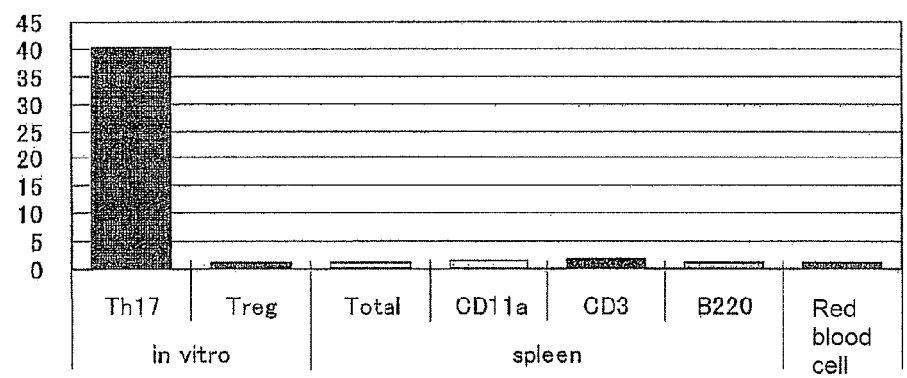

The results are shown in FIG. 5. While the expression levels of Embigin in B cell, leukocyte, CD3 positive cell, red blood cell and Treg cell are extremely low, Embigin is highly expressed on the cellular membrane surface of Th17 cell as compared to these cells. Thus, it has been found that Th17 cell can be detected by examining the expression of Embigin.

Example 4

Investigation of Embigin Expression in Human Th17 Cell

Expression of Embigin on human Th17 cellular membrane surface was evaluated by flow cytometry.

Human Th17 cell differentiated from peripheral blood was treated in a medium containing Phorbol 12-Myristate 13-Acetate, ionomycin and BD GolgiStop (Becton, Dickinson and Company) for 4 hr, and stained with culture supernatants of anti-human Embigin antibody producing clones 6G1E6, 7C4E10 and PE-labeled goat anti-mouse Ig antibody (Beckman Coulter, Inc.) as a secondary antibody. As a negative control of the anti-human Embigin antibody, the cells were stained with mouse IgG (Becton, Dickinson and Company) in the same manner. Furthermore, the cells were stained with APC-labeled anti-CD4 antibody. These samples were subjected to permealization using BD Cytofix/Cytoperm Fixation/Permeabilization Solution kit (Becton, Dickinson and Company), and stained with FITC-labeled anti-human IL-17 antibody. These samples were evaluated by flow cytometry. The flow cytometer used was FACS Calibur (Becton, Dickinson and Company). A gate was set on a living cell population using forward scatter and side scatter histograms, and $CD4^+IL17^+$ cell was analyzed as Th17 cell.

Figure 7:
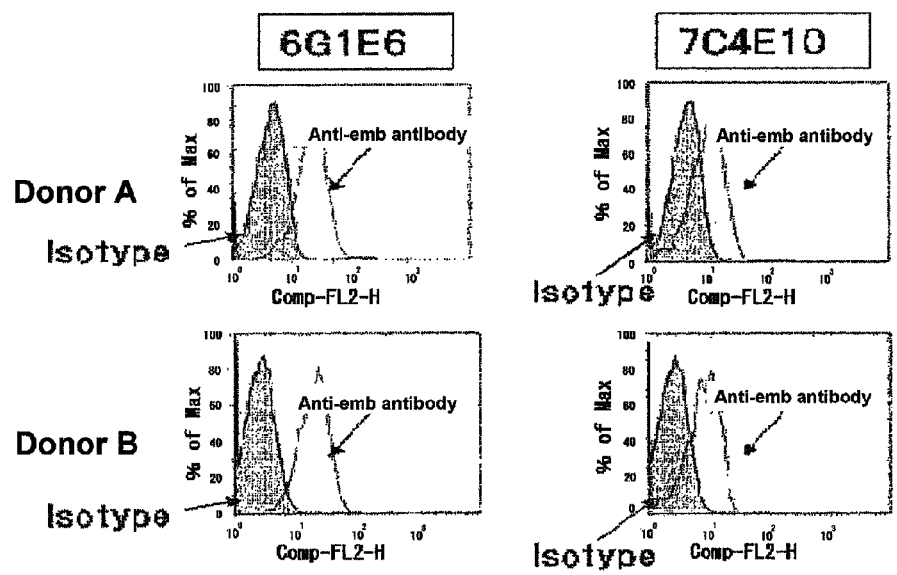
FIG. 7 is a figure showing evaluation of Embigin expression on human Th17 cellular membrane surface by flow cytometry. Isotype (rat IgG) was 5 μg/mL concentration, and a culture supernatant was used as the anti-Embigin antibody (anti-emb antibody).

The results are shown in FIG. 7. It has been found that Embigin is expressed in human Th17 cell.

Example 5

Selective Depletion (Cell Death) of Mouse Th17 Cell Using Toxin-Modified Anti-Embigin Antibody Whether Th17 cell selective depletion (cell death) using anti-Embigin antibody is possible was evaluated by using pathogenic cells.

The pathogenic cells were prepared by reference to J. Exp. Med. (2005) 201; 233-240.

In other words, SJL mouse (5-week-old, CHARLES RIVER LABORATORIES JAPAN, INC.) was immunized with PLP peptide (SEQ ID NO: 7) together with Freund's complete adjuvant and lymph node cells were collected 10 days later. After cultivating in the presence of PLP and IL-23 for 5 days, the cells were further cultivated in the presence of IL-23 and IL-2 for 3-5 days to give pathogenic cells.

CD4+T cells were prepared from the prepared pathogenic cells by using CD4+ T cell isolation kit (Miltenyi Biotec K.K.).

A cell removal operation was performed by culturing in a medium containing IL-23, IL-2, anti-mouse Embigin antibody (2G21, 3E64), Anti-IgG, Rat, Goat-Poly, Saporin <Rat-ZAP> (Advanced Targeting Systems) for 36 hr. As a control, the cells were treated in the same manner using rat IgG instead of anti-mouse Embigin antibody. The cells after reaction were treated in a medium containing Phorbol 12-Myristate 13-Acetate, ionomycin, and BD GolgiStop (Becton, Dickinson and Company) for 4 hr, and stained with Per-CP-labeled anti-mouse CD4 antibody (COSMO BIO CO., LTD.), PE-labeled anti-mouse IFNγ antibody (BD Biosciences), and Alexa488-labeled anti-mouse IL17 antibody (BD Pharmingen). These samples were evaluated by flow cytometry. The flow cytometer used was FACS Calibur (Becton, Dickinson and Company). CD4+IL17+ cells were classified as Th17 cell, CD4+IFNγ+IL17− cells were classified as Th1 cell, and CD4+IFNγ−IL17− cells were classified as other, and the survival cell rate was evaluated based on the measured value of each cell population in the control group as 100%.

Figure 8:
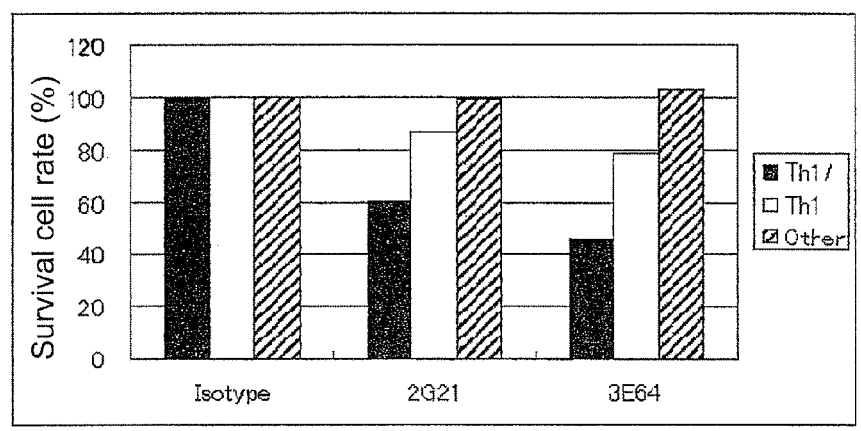
FIG. 8 is a figure showing evaluation of cell depletion specificity of a toxin-modified anti-Embigin antibody in pathogenic cells.

The results are shown in FIG. 8. Since the survival cell rate of Th17 cell remarkably decreased as compared to that of Th1 cell and other cells, it has been found that anti-Embigin antibody modified with saporin, which is one kind of toxin, selectively depletes Th17 cell.

Example 6

Selective Depletion of Th17 Cell by Anti-Mouse IgG-Conjugated Magnetic Beads

Whether Th17 cell selective depletion (cell death) using anti-Embigin antibody is possible was evaluated by using pathogenic cells.

CD4+T cells were prepared from pathogenic cells prepared in the same manner as in Example 5 and using CD4+ T cell isolation kit (Miltenyi Biotec K.K.).

The pathogenic cells and anti-mouse Embigin antibody (2G23 or 3E66) were mixed at 4° C. for 30 min and centrifuged (1000 rpm, 3 min) to recover the cells. Anti-rat IgG antibody-modified magnetic beads (Dynal) were added to the recovered cells, and they were mixed at 4° C. for 30 min. An operation to remove cells bound with the magnetic beads by a magnet was repeated twice, and the cells not bound with the magnetic beads were recovered. As a control, rat IgG was used instead of the anti-mouse Embigin antibody. As the control, a cell free of the cell removal operation was used.

These cells were treated in a medium containing Phorbol 12-Myristate 13-Acetate, ionomycin and BD GolgiStop (Becton, Dickinson and Company) for 4 hr, and stained with Per-CP-labeled anti-mouse CD4 antibody (COSMO BIO CO., LTD.), PE-labeled anti-mouse IFNγ antibody (BD Biosciences) and Alexa488-labeled anti-mouse IL17 antibody (BD Pharmingen). These samples were evaluated by flow cytometry. The flow cytometer used was FACS Calibur (Becton, Dickinson and Company). CD4+IL17+ cell was classified as Th17 cell, CD4+IFNγ+IL17− cell was classified as Th1 cell, and CD4+IFNγ−IL17− cell was classified as other, and the survival cell rate was evaluated based on the measured value of each cell population in the control group as 100%.

Figure 9:
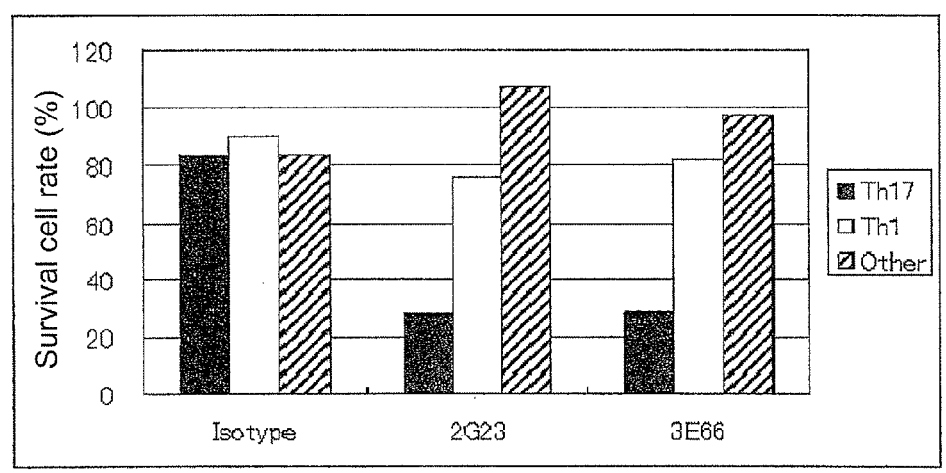
FIG. 9 is a figure showing evaluation of cell depletion specificity of an anti-Embigin antibody in pathogenic cells.

The results are shown in FIG. 9. Since the survival cell rate of Th17 cell remarkably decreased as compared to that of Th1 cell and other cells, it was found that Th17 cell was selectively depleted.

Example 7

Expression of Embigin in Mouse Tissue (Tissue Panel)

Each mouse tissue protein blot such as INSTA-Blot Mouse Tissue (IMGENEX) and the like is used, and reacted with an anti-mouse Embigin antibody (IMGENEX) and HRP-labeled goat anti-rabbit Ig antibody (BIOSOURCE) to perform Western blotting. The detection is performed using ECL Plus Western Blotting Detection System (GE Healthcare Japan) and LAS-3000 (Fujifilm).

Example 8

Investigation of Expression of Embigin in Other than Human Th17 Cell

Comparison of the expression levels of Embigin in various human cells is possible by the following method.

CD4+CD25+T cells are separated from human peripheral blood by Dynabeads Regulatory CD4+CD25+ T Cell Kit (Invitrogen) and expansion cultured using Dynabeads Human Treg Expander (Invitrogen) to prepare human Treg cells, which are subjected to the test. The human Treg cell is stained with culture supernatants of anti-human Embigin antibody producing clones 6G1E6, 7C4E10 and PE-labeled goat anti-mouse Ig antibody (Beckman Coulter, Inc.) as a secondary antibody. As a negative control of the anti-human Embigin antibody, the cells are stained with mouse IgG (Becton, Dickinson and Company) in the same manner. These samples are analyzed by flow cytometer FACS Calibur (Becton, Dickinson and Company).

In addition, the cell in the human peripheral blood is stained with culture supernatants of anti-human Embigin antibody producing clones 6G1E6, 7C4E10 and PE-labeled goat anti-mouse Ig antibody (Beckman Coulter, Inc.) as a secondary antibody. As a negative control of the anti-human Embigin antibody, the cells are stained with mouse IgG (Becton, Dickinson and Company) in the same manner. These samples are analyzed by flow cytometer FACS Calibur (Becton, Dickinson and Company). When various cells in the peripheral blood are subanalyzed, cells are stained with APC-labeled anti-CD4 antibody to identify CD4 positive cell, or cells are stained with APC-labeled anti-DX5 antibody to identify NK cell, or cells are stained with APC-labeled anti-CD11c antibody to identify dendritic cell, or cells are stained with APC-labeled anti-CD8 antibody to identify CD8 positive cell, or cells are stained with APC-labeled anti-CD11b antibody to identify macrophage, or cells are stained with APC-labeled anti-B220 antibody to identify B cell, each followed by analysis by flow cytometry.

Example 9

Confirmation of Depletion of Th17 Cell In Vivo

Selective depletion of Th17 cell in vivo can be confirmed by the method described in J. Exp. Med. (2005) 201; 233-240.

Pathogenic cell prepared by a method similar to that in Example 5 is labeled with 5- or 6-(N-Succinimidyloxycarbonyl)-fluorescein 3',6'-diacetate (CFSE, DOJINDO LABORATORIES).

CFSE-labeled cell is transferred into a mouse via the tail vein, and toxin-modified anti-mouse Embigin antibody is administered. As a control, the cells are treated in the same manner using rat IgG instead of toxin-modified anti-mouse Embigin antibody. After 4 hr-4 days, cells are recovered from peripheral blood, spleen, central nerve, lymphoid tissue and the like. The obtained cells are treated in a medium containing Phorbol 12-Myristate 13-Acetate, ionomycin and BD GolgiStop (Becton, Dickinson and Company) for 4 hr, and stained with Per-CP-labeled anti-mouse CD4 antibody (COSMO BIO CO., LTD.), PE-labeled anti-mouse IFNγ antibody (BD Biosciences) or PE-labeled anti-mouse IL17 antibody (BD Pharmingen). These samples are evaluated by flow cytometry. A gate is set on a living cell population and CFSF positive cell, $CD4^+IL17^+$ cells are classified as Th17 cell, $CD4^+IFN\gamma^+IL17^-$ cells are classified as Th1 cell, and $CD4^+IFN\gamma^-IL17^-$ cells are classified as other, and the survival cell rate is evaluated based on the measured value of each cell population in the control group as 100%.

Example 10

Confirmation of Onset Suppressive Action by Depletion of Th17 Cell Ex Vivo

The onset suppressive action by selective depletion of Th17 cell in autoimmune disease model can be confirmed by the method shown below.

In the same manner as in Examples 5, $CD4^+T$ cells are prepared from pathogenic cells by using $CD4^+T$ cell isolation kit (Miltenyi Biotec K.K.). A cell removal operation is performed by culturing in a medium containing IL-23, IL-2, anti-mouse Embigin antibody (2G21, 3E64), Anti-IgG, Rat, Goat-Poly, Saporin <Rat-ZAP> (Advanced Targeting Systems) for 36 hr. As a control, rat IgG is used instead of anti-mouse Embigin antibody. Alternatively, it is also possible by specifically eliminating Th17 by using magnetic beads as in Example 6.

The cell after cell removal operation is administered to a mouse from the tail vein to the control group at $3\times10^6$ cells/head. Paralysis of the four limbs and tail, and the body weight are observed over time, and EAE (experimental autoimmune encephalomyelitis) symptom is evaluated.

Example 11

Confirmation of Onset Suppressive Action by Depletion of Th17 Cell by Antibody Administration In an autoimmune disease model, the suppressive action for disease onset by selective depletion of Th17 cell can be confirmed by the method shown below.

In the same manner as in Examples 5, $CD4^+T$ cells are prepared from pathogenic cells by using $CD4^+T$ cell isolation kit (Miltenyi Biotec K.K.). The cell is administered to a mouse from the tail vein at $3\times10^6$ cells/head.

An anti-Embigin antibody having a cell depleting ability (for example, saporinized antibody, ADCC activity possessing antibody and the like) is administered to a mouse simultaneously with cell transfer or after the onset and the like, and paralysis of the four limbs and tail, and the body weight are observed over time, based on which the action on the onset of EAE is evaluated.

Alternatively, a peptide such as PLP or MOG and the like is administered to mouse or rat used widely to prepare EAE model according to the methods described in Methods Mol Biol. 2009; 549:157-73., Brain (2004); 127:2201-2213, an anti-Embigin antibody having a cell depleting ability (for example, saporinized antibody, antibody possessing ADCC activity and the like) is administered simultaneously with peptide administration, before the onset of EAE and the like, and the action on the onset of EAE is evaluated.

Example 12

Confirmation of Suppressive Action for Relapse by Depletion of Th17 Cell

Since many of the autoimmune diseases show repeats of a stage of aggravation of symptom and a stage of remittance, suppression of relapse is important for the treatment.

This point can be confirmed using, for example, an EAE model.

An anti-Embigin antibody is administered to EAE models described in Methods Mol Biol. 2009; 549:157-73., Brain (2004); 127:2201-2213 and the like after the onset of EAE or after EAE symptoms subside, and an efficacy on the relapse is evaluated.

Example 13

Investigation of Embigin Expression in Mouse Tissue

To investigate expression of Embigin in each tissue of mouse, INSTA-Blot Mouse Tissue (IMGENEX) was used as each mouse tissue protein blot, which was reacted with an anti-mouse Embigin antibody (IMGENEX) and HRP-labeled goat anti-rabbit Ig antibody (BIOSOURCE) to perform Western blotting. The detection was performed using ECL Plus Western Blotting Detection System (GE Healthcare Japan) and LAS-3000 (Fujifilm).

Figure 10:
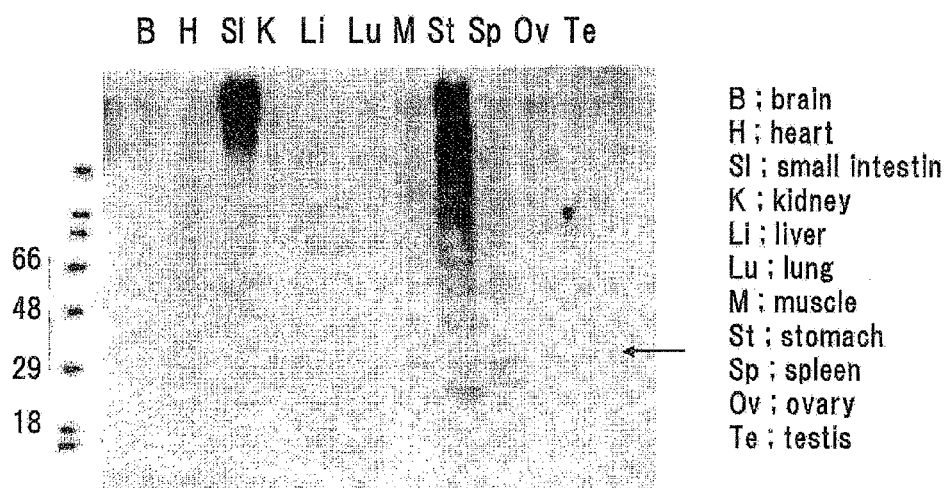
FIG. 10 is a figure showing evaluation of mouse Embigin expression amounts of various organs of a mouse by Western blotting and using a commercially available organ panel. A commercially available rabbit anti-mouse Embigin antibody was used at $1/1000$-fold dilution.

The results are shown in FIG. 10. Although the expression of Embigin was confirmed in the muscle and spleen, the expression level thereof was very low, and no tissue strongly expressed Embigin. Therefore, a therapeutic agent containing an anti-Embigin antibody is expected to show fewer side effects on each tissue of the body.

Example 14

Confirmation of Depletion of Th17 Cell In Vivo

Selective depletion of Th17 cell in vivo was confirmed according to the method described in J. Exp. Med. (2005) 201; 233-240.

A 5-week-old female SJL/J mouse was immunized with PLP partial peptide ($PLP_{139-151}$, SEQ ID NO: 7) together with Freund's complete adjuvant and lymph node cells were prepared 10 days later. After cultivating in the presence of PLP and IL-23 for 5 days, the cells were further cultivated in the presence of IL-23 and IL-2 for 3-5 days to give pathogenic cells. $CD4^+T$ cell was prepared from the pathogenic cell by using $CD4^+$ T cell isolation kit (Miltenyi Biotec K.K.). This cell population contains 30-50% of Th17 cells. This pathogenic cell was labeled with carboxyfluorescein diacetate succinimidyl ester (CFSE) by CellTrace CFSE Cell Proliferation Kit for flow cytometry (Invitrogen). An anti-mouse Embigin antibody (3E64D1) was administered to a mouse, and CFSE-labeled cell was transferred to a mouse from the tail vein at $1.5\times10^7$ cells. As a control, rat IgG2b was used. One day later, the cell was obtained from the spleen. The obtained cell was evaluated by flow cytometry. The number of CFSE positive cell was calculated, and the decrease to the CFSE positive cell number in the control group as 100% was evaluated as a cell depleting rate.

Figure 11:
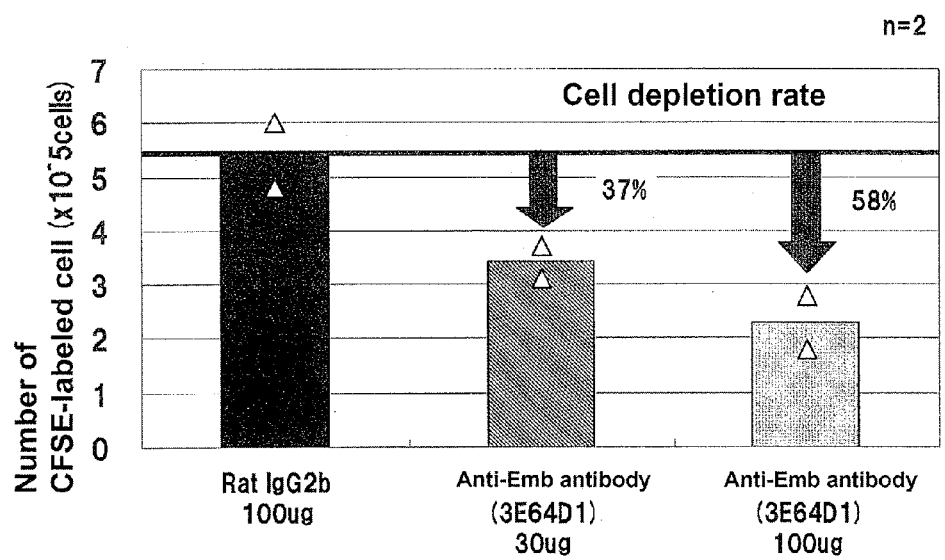
FIG. 11 is a figure showing evaluation of the effect of administration of an anti-Embigin antibody (anti-Emb antibody) on the cell number of fluorescence-labeled pathogenic cells transferred to the mouse spleen. The CFSE-labeled pathogenic cells of the mouse were $1.5 \times 10^7$ cells, and 30 μg or 100 μg of the anti-Embigin antibody was used. Flow cytometry was used for detection of the number of the fluorescent cells. In the Figure, Δ shows the measurement value of each individual.

The results are shown in FIG. 11. It was confirmed that the number of transferred CFSE positive cells decreased in a dose-dependent manner by the administration of the anti-Embigin antibody. This result has shown that an anti-Embigin antibody can decrease the number of Th17 cells by the ADCC and CDC activity of the antibody. It has been found that administration of an anti-Embigin antibody to an individual can decrease the number of Th17 cells in vivo.

Example 15

Confirmation of Onset Suppressive Action by Depletion of Th17 Cell Ex Vivo

In an autoimmune disease model, an onset suppressive action by selective depletion of Th17 cell was confirmed by the method shown below.

Figure 12:
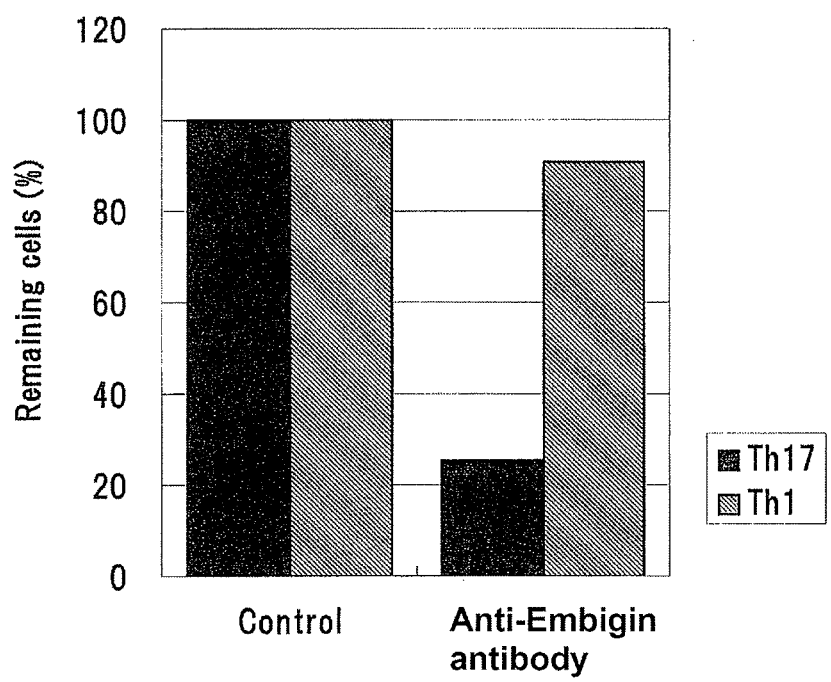
FIG. 12 is a figure showing evaluation of cell depletion specificity of an anti-Embigin antibody in pathogenic cells.

A 5-week-old female SJL/J mouse was immunized with PLP partial peptide ($PLP_{139-151}$) together with Freund's complete adjuvant and lymph node cells were prepared 10 days later. After cultivating in the presence of PLP and IL-23 for 5 days, the cells were further cultivated in the presence of IL-23 and IL-2 for 3-5 days to give pathogenic cells. $CD4^+$ T cell was prepared from the pathogenic cell by using $CD4^+$ T cell isolation kit (Miltenyi Biotec K.K.). A cell removal operation was performed by culturing in a medium containing IL-23, IL-2, anti-mouse Embigin antibody (3E64D1) 1 µg/mL, Anti-IgG, Rat, Goat-Poly, Saporin <Rat-ZAP> (Advanced Targeting Systems) for 36 hr. As a control, rat IgG2b was used instead of the anti-mouse Embigin antibody. A part of the cells after the reaction was treated in a medium containing Phorbol 12-Myristate 13-Acetate, ionomycin, BD GolgiStop (Becton, Dickinson and Company) for 4 hr, and the cells were stained with Per-CP-labeled anti-mouse CD4 antibody (COSMO BIO CO., LTD.), PE-labeled anti-mouse IFNγ antibody (BD Biosciences) and Alexa488-labeled anti-mouse IL17 antibody (BD Pharmingen). These samples were evaluated by flow cytometry. The flow cytometer used was FACS Calibur (Becton, Dickinson and Company). $CD4^+IL17^+$ cells were classified as Th17 cell, and $CD4^+IFN\gamma^+IL17^-$ cells as Th1 cell, and the survival cell rate was evaluated based on the measured value of each cell population in the control group as 100%. Th17 cell selective cell depletion could be confirmed. The results are shown in FIG. 12.

The cell after cell removal operation or the cell of the control group was transferred to a mouse from the tail vein at $3 \times 10^6$ cell/head, and paralysis of the four limbs and tail, and the body weight were observed over time, based on which the symptom of experimental autoimmune encephalomyelitis (EAE) was evaluated. The level of the severity of the symptom is shown in scores according to the following criteria.

Figure 13:
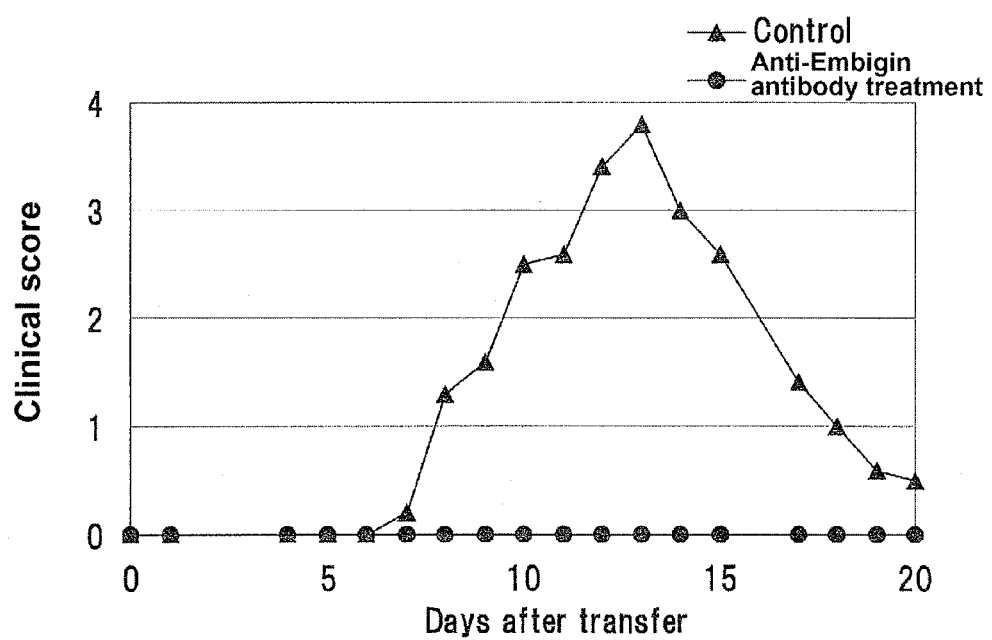
FIG. 13 is a figure showing evaluation of the clinical score of a multiple sclerosis model by transferring cells after selectively depleting Th17 cells with an anti-Embigin antibody into a mouse. The transfers of cells were $3 \times 10^6$ cells, and 1 μg/mL of an anti-Embigin antibody was used. The clinical score was evaluated until day 20 after cell transfer.

0: without symptom
0.5: mild paralysis of tail
1: paralysis of tail
2: mild paralysis of hindpaw
3: moderate to severe paralysis of hindpaw, or mild paralysis of forelimb
4: complete paralysis of hindpaw, or moderate to severe paralysis of forelimb
5: paralysis of four limbs or in life-or-death crisis phase
6: death The results are shown in FIG. 13. EAE symptom was completely suppressed by selective depletion of Th17 cell using an anti-Embigin antibody.

Example 16

Confirmation of Onset Suppressive Action by Depletion of Th17 Cell by Antibody Administration Using an active EAE onset model, which is an autoimmune disease model, an EAE onset suppressive action of an anti-Embigin antibody was confirmed.

(1) Preparation of Active EAE Onset Model

EAE mouse, which is an animal model of multiple sclerosis, was used. EAE was provoked by the method of SD. Miller et al. (Curr. Protoc. Immunol. 2010; 88:15.1.1-15.1.20.). That is, PLP partial peptide ($PLP_{139-151}$) (150 µg) admixed with Freund's complete adjuvant was subcutaneously injected to the lower back of 9-week-old female SJL/J mouse (purchased from CHARLES RIVER). Paralysis of the four limbs and tail, and the body weight are observed over time and EAE symptom was evaluated.

The score of EAE symptom followed Example 15.

(2) Administration of Antibody and Evaluation of Prevention for Disease Onset

An anti-Embigin antibody (3E64D1) was suspended in a PBS solution and intravenously administered to the mouse prepared in the above-mentioned (1) at 0.3 µg per mouse. Rat IgG2b was intravenously administered to the control group. Administration was performed once per day on day 7 and day 14 after peptide sensitization. Paralysis of the four limbs and tail, and the body weight are observed over time, and the EAE symptom was evaluated.

Figure 14:
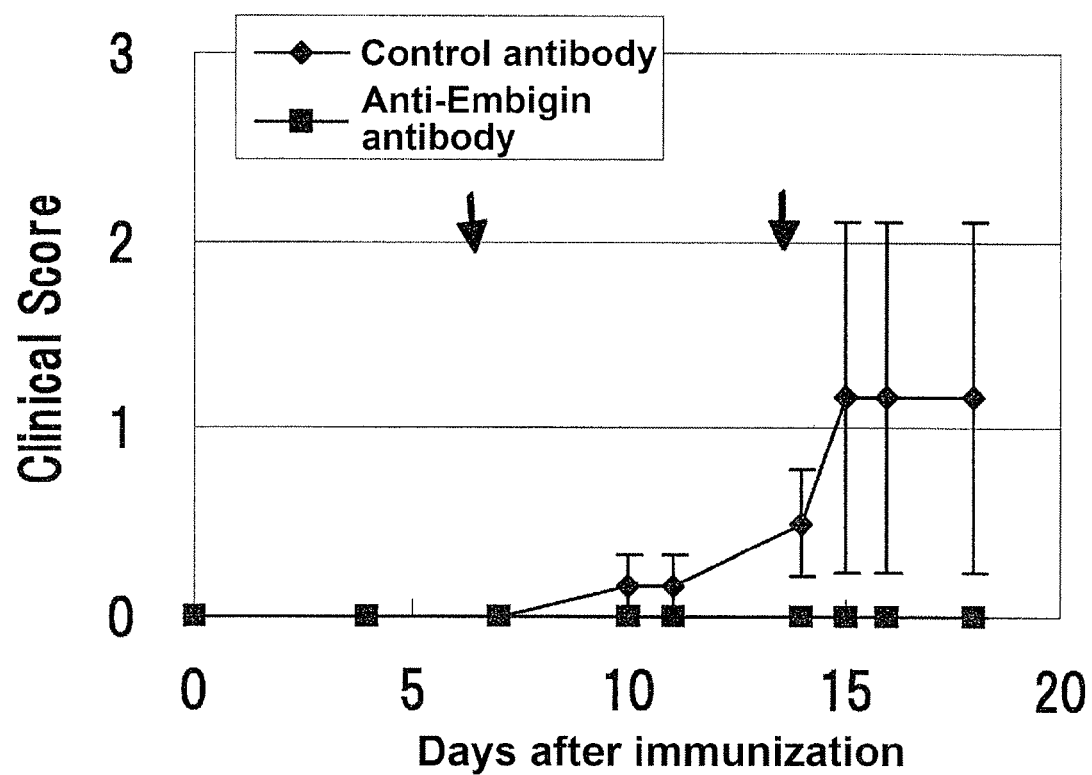
FIG. 14 is a figure showing evaluation of an efficacy, on clinical score, of administration of, before onset of pathology, an anti-Embigin antibody to a mouse induced to make a multiple sclerosis model by immunizing with PLP. PLP was mixed with Freund's complete adjuvant and subcutaneously immunized once. The anti-Embigin antibody (300 μg) was administered twice on days 7 and 14 (shown by arrows) after immunization. The clinical score was evaluated until day 18 after PLP immunization.

The results are shown in FIG. 14. The administration of the anti-Embigin antibody completely suppressed the onset of the EAE pathology. The results have shown that an anti-Embigin antibody can suppress the onset of multiple sclerosis (MS).

Example 17

Confirmation of Suppressive Action for Relapse by Depletion of Th17 Cell

Since many of the autoimmune diseases show repeats of a stage of aggravation of symptom and a stage of remittance, suppression of relapse is important for the treatment.

This point was confirmed using an EAE model. An anti-Embigin antibody was administered to EAE models described in Methods Mol Biol. 2009; 549:157-73., Brain (2004); 127:2201-2213 and the like after the onset of EAE, and an efficacy on the relapse was evaluated. The animals that showed the onset on day 12 after peptide sensitization were grouped using the clinical score and body weight as indices. An anti-Embigin antibody (3E64D1) was intravenously administered once per day on day 12 of peptide immunization immediately after grouping and day 19. Thereafter, the action on the EAE symptom was evaluated. The score of EAE symptom followed the standard shown in Example 15.

Figure 15:
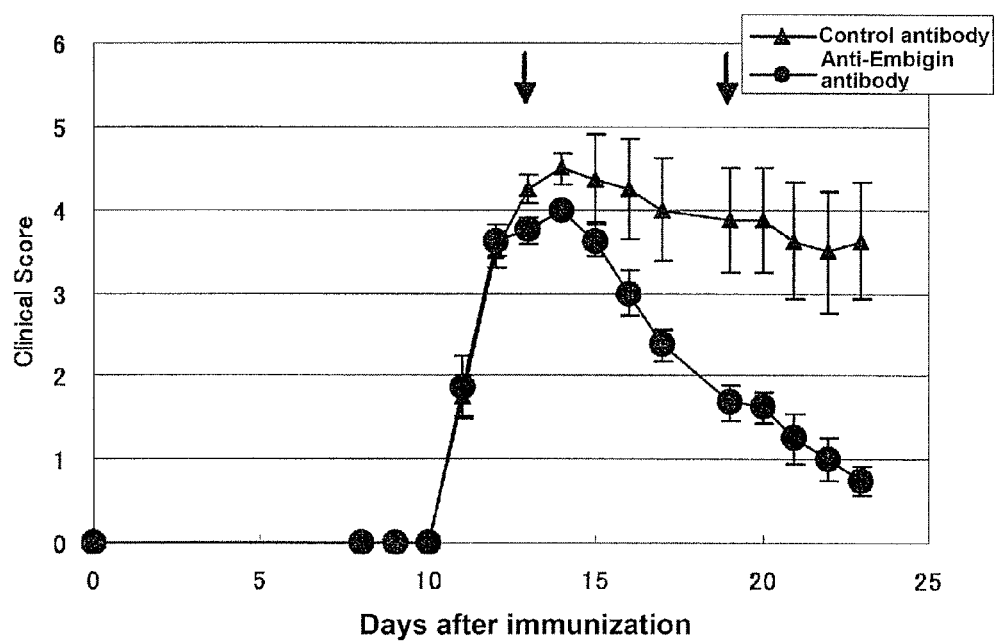
FIG. 15 is a figure showing evaluation of an efficacy, on clinical score, of administration of, after onset of pathology, an anti-Embigin antibody to a mouse induced to make a multiple sclerosis model by immunizing with PLP. PLP was mixed with Freund's complete adjuvant and subcutaneously immunized once. The mice that developed pathology were grouped on day 12 from PLP immunization based on the clinical score, and an anti-Embigin antibody (100 μg) was administered twice on the grouping day and 7 days after the grouping (shown by arrows). The clinical score was evaluated until day 23 after PLP immunization.

The results are shown in FIG. 15. It was confirmed that administration of an anti-Embigin antibody rapidly decreases the clinical score. Exacerbation observed on day 23 in the control was not observed. This result has shown that an anti-Embigin antibody promotes induction of remission of multiple sclerosis (MS) and suppresses exacerbation, and therefore, it can be used as a remission inducing agent or an exacerbation suppressing agent for multiple sclerosis.

INDUSTRIAL APPLICABILITY

According to the present invention, a therapeutic agent for autoimmune diseases such as multiple sclerosis and the like and allergic diseases, and a cytotoxic agent to Th17 cell can be provided. Furthermore, the present invention can also provide an anti-Embigin antibody useful for a drug delivery system that can selectively and efficiently deliver a drug and the like to Th17 cell, a Th17 cell marker, a reagent for Th17 cell detection, and a convenient Th17 cell detection method.

This application is based on a patent application No. 2010-127316 filed in Japan (filing date: Jun. 2, 2010), the contents of which are incorporated in full herein.

---

The invention claimed is:

1. A method for the prophylaxis and/or therapy of a disease associated with Th17 cells in a subject, comprising administering an effective amount of an anti-Embigin antibody having cytotoxicity or cytotoxicity inducing activity to the subject, wherein the disease associated with Th17 cells is selected from the group consisting of multiple sclerosis, psoriasis, rheumatism, chronic noninfectious uveitis, and glomerulonephritis.

2. The method according to claim 1, wherein the anti-Embigin antibody has cytotoxicity inducing activity.

3. The method according to claim 2, wherein the subclass of the anti-Embigin antibody having cytotoxicity inducing activity is IgG1, IgG3 or IgM.

4. The method according to claim 1, wherein the anti-Embigin antibody has cytotoxicity.

5. The method according to claim 4, wherein the anti-Embigin antibody having cytotoxicity is conjugated with a cytotoxic substance, a chemotherapeutic agent or a radioisotope.

6. The method according to claim 1, wherein the disease is multiple sclerosis.

7. A method for delivering a cytotoxic drug to a Th17 cell in a subject with a disease associated with Th17 cells, comprising administering to the subject an anti-Embigin antibody conjugated with the cytotoxic drug, wherein the disease associated with Th17 cells is selected from the group consisting of multiple sclerosis, psoriasis, rheumatism, chronic noninfectious uveitis, and glomerulonephritis.

8. The method according to claim 7, wherein the cytotoxic drug is a cytotoxic substance, a chemotherapeutic agent or a radioisotope.

* * * * *

SEQUENCE LISTING

<160> NUMBER OF SEQ ID NOS: 9

<210> SEQ ID NO 1
<211> LENGTH: 327
<212> TYPE: PRT
<213> ORGANISM: Homo sapiens

<400> SEQUENCE: 1

```
Met Arg Ala Leu Pro Gly Leu Leu Glu Ala Arg Ala Arg Thr Pro Arg
1               5                   10                  15

Leu Leu Leu Leu Gln Cys Leu Leu Ala Ala Arg Pro Ser Ser Ala
            20                  25                  30

Asp Gly Ser Ala Pro Asp Ser Pro Phe Thr Ser Pro Pro Leu Arg Glu
        35                  40                  45

Glu Ile Met Ala Asn Asn Phe Ser Leu Glu Ser His Asn Ile Ser Leu
    50                  55                  60

Thr Glu His Ser Ser Met Pro Val Glu Lys Asn Ile Thr Leu Glu Arg
65                  70                  75                  80

Pro Ser Asn Val Asn Leu Thr Cys Gln Phe Thr Thr Ser Gly Asp Leu
                85                  90                  95

Asn Ala Val Asn Val Thr Trp Lys Lys Asp Gly Glu Gln Leu Glu Asn
            100                 105                 110

Asn Tyr Leu Val Ser Ala Thr Gly Ser Thr Leu Tyr Thr Gln Tyr Arg
        115                 120                 125

Phe Thr Ile Ile Asn Ser Lys Gln Met Gly Ser Tyr Ser Cys Phe Phe
    130                 135                 140

Arg Glu Glu Lys Glu Gln Arg Gly Thr Phe Asn Phe Lys Val Pro Glu
145                 150                 155                 160

Leu His Gly Lys Asn Lys Pro Leu Ile Ser Tyr Val Gly Asp Ser Thr
                165                 170                 175

Val Leu Thr Cys Lys Cys Gln Asn Cys Phe Pro Leu Asn Trp Thr Trp
            180                 185                 190

Tyr Ser Ser Asn Gly Ser Val Lys Val Pro Val Gly Val Gln Met Asn
        195                 200                 205

Lys Tyr Val Ile Asn Gly Thr Tyr Ala Asn Glu Thr Lys Leu Lys Ile
    210                 215                 220

Thr Gln Leu Leu Glu Glu Asp Gly Glu Ser Tyr Trp Cys Arg Ala Leu
225                 230                 235                 240

Phe Gln Leu Gly Glu Ser Glu His Ile Glu Leu Val Val Leu Ser
                245                 250                 255

Tyr Leu Val Pro Leu Lys Pro Phe Leu Val Ile Val Ala Glu Val Ile
            260                 265                 270

Leu Leu Val Ala Thr Ile Leu Leu Cys Glu Lys Tyr Thr Gln Lys Lys
        275                 280                 285

Lys Lys His Ser Asp Glu Gly Lys Glu Phe Glu Gln Ile Glu Gln Leu
    290                 295                 300

Lys Ser Asp Asp Ser Asn Gly Ile Glu Asn Asn Val Pro Arg His Arg
305                 310                 315                 320
```

Lys Asn Glu Ser Leu Gly Gln
            325

<210> SEQ ID NO 2
<211> LENGTH: 984
<212> TYPE: DNA
<213> ORGANISM: Homo sapiens

<400> SEQUENCE: 2

```
atgcgcgccc tccccggcct gctggaggcc agggcgcgta cgccccggct gctcctcctc      60
cagtgccttc tcgctgccgc gcgcccaagc tcggcggacg gcagtgcccc agattcgcct     120
tttacaagtc cacctctcag agaagaaata atggcaaata actttccctt ggagagtcat     180
aacatatcac tgactgaaca ttctagtatg ccagtagaaa aaaatatcac tttagaaagg     240
ccttctaatg taaatctcac atgccagttc acaacatctg gggatttgaa tgcagtaaat     300
gtgacttgga aaaagatgg tgaacaactt gagaataatt atcttgtcag tgcaacagga     360
agcaccttgt atacccaata caggttcacc atcattaata gcaaacaaat gggaagttat     420
tcttgtttct ttcgagagga aaaggaacaa aggggaacat ttaatttcaa agtccctgaa     480
cttcatggga aaaacaagcc attgatctct tacgtagggg attctactgt cttgacatgt     540
aaatgtcaaa attgttttcc tttaaattgg acctggtaca gtagtaatgg gagtgtaaag     600
gttcctgttg tgttcaaat gaataaatat gtgatcaatg aacatatgc taacgaaaca     660 aagctgaaga taacacaact tttggaggaa gatggggaat cttactggtg ccgtgcacta     720
ttccaattag gcgagagtga agaacacatt gagcttgtgg tgctgagcta tttggtgccc     780
ctcaaaccat ttcttgtaat agtggctgag gtgattcttt tagtggccac cattctgctt     840
tgtgaaaagt acacacaaaa gaaaaagaag cactcagatg aggggaaaga atttgagcag     900
attgaacagc tgaaatcaga tgatagcaat ggtatagaaa ataatgtccc caggcataga     960
aaaaatgagt ctctgggcca gtga                                            984
```

<210> SEQ ID NO 3
<211> LENGTH: 24
<212> TYPE: DNA
<213> ORGANISM: Artificial Sequence
<220> FEATURE:
<223> OTHER INFORMATION: Synthetic embigin primer

<400> SEQUENCE: 3
gtacatgggt aatgaaaccg caca                                              24

<210> SEQ ID NO 4
<211> LENGTH: 22
<212> TYPE: DNA
<213> ORGANISM: Artificial Sequence
<220> FEATURE:
<223> OTHER INFORMATION: Synthetic embigin primer

<400> SEQUENCE: 4
gcacaaccag ctcattctgc tc                                                22

<210> SEQ ID NO 5
<211> LENGTH: 24
<212> TYPE: DNA
<213> ORGANISM: Artificial Sequence
<220> FEATURE:
<223> OTHER INFORMATION: Synthetic 36B4 primer

<400> SEQUENCE: 5

-continued

```
gaggaatcag atgaggatat ggga                                              24
```

<210> SEQ ID NO 6
<211> LENGTH: 20
<212> TYPE: DNA
<213> ORGANISM: Artificial Sequence
<220> FEATURE:
<223> OTHER INFORMATION: Synthetic 36B4 primer

<400> SEQUENCE: 6

```
aagcaggctg acttggttgc                                                   20
```

<210> SEQ ID NO 7
<211> LENGTH: 13
<212> TYPE: PRT
<213> ORGANISM: Artificial Sequence
<220> FEATURE:
<223> OTHER INFORMATION: Synthetic PLP peptide

<400> SEQUENCE: 7

His Ser Leu Gly Lys Trp Leu Gly His Pro Asp Lys Phe
1               5                   10

<210> SEQ ID NO 8
<211> LENGTH: 330
<212> TYPE: PRT
<213> ORGANISM: Mus musculus

<400> SEQUENCE: 8

Met Arg Ser His Thr Gly Leu Arg Ala Leu Val Ala Pro Gly Tyr Pro
1               5                   10                  15

Leu Leu Leu Leu Cys Leu Leu Ala Ala Thr Arg Pro Asp Pro Ala Glu
                20                  25                  30

Gly Asp Pro Thr Asp Pro Thr Phe Thr Ser Leu Pro Val Arg Glu Glu
            35                  40                  45

Met Met Ala Lys Tyr Ser Asn Leu Ser Leu Lys Ser Cys Asn Ile Ser
        50                  55                  60

Val Thr Glu Lys Ser Asn Val Ser Val Glu Glu Asn Val Ile Leu Glu
65                  70                  75                  80

Lys Pro Ser His Val Glu Leu Lys Cys Val Tyr Thr Ala Thr Lys Asp
                85                  90                  95

Leu Asn Leu Met Asn Val Thr Trp Lys Lys Asp Asp Glu Pro Leu Glu
            100                 105                 110

Thr Thr Gly Asp Phe Asn Thr Thr Lys Met Gly Asn Thr Leu Thr Ser
        115                 120                 125

Gln Tyr Arg Phe Ile Val Phe Asn Ser Lys Gln Leu Gly Lys Tyr Ser
    130                 135                 140

Cys Val Phe Gly Glu Lys Glu Leu Arg Gly Thr Phe Asn Ile His Val
145                 150                 155                 160

Pro Lys Ala His Gly Lys Lys Lys Ser Leu Ile Ala Tyr Val Gly Asp
                165                 170                 175

Ser Thr Val Leu Lys Cys Val Cys Gln Asp Cys Leu Pro Leu Asn Trp
            180                 185                 190

Thr Trp Tyr Met Gly Asn Glu Thr Ala Gln Val Pro Ile Asp Ala His
        195                 200                 205

Ser Asn Glu Lys Tyr Ile Ile Asn Gly Ser His Ala Asn Glu Thr Arg
    210                 215                 220

Leu Lys Ile Lys His Leu Leu Glu Glu Asp Gly Gly Ser Tyr Trp Cys
225                 230                 235                 240

-continued

```
Arg Ala Thr Phe Gln Leu Gly Glu Ser Glu Glu Gln Asn Glu Leu Val
                245                 250                 255

Val Leu Ser Phe Leu Val Pro Leu Lys Pro Phe Leu Ala Ile Leu Ala
            260                 265                 270

Glu Val Ile Leu Leu Val Ala Ile Ile Leu Leu Cys Glu Val Tyr Thr
        275                 280                 285

His Lys Lys Lys Asn Asp Pro Asp Ala Gly Lys Glu Phe Glu Gln Ile
    290                 295                 300

Glu Gln Leu Lys Ser Asp Asp Ser Asn Gly Ile Glu Asn Asn Val Pro
305                 310                 315                 320

Arg Tyr Arg Lys Thr Asp Ser Ala Asp Gln
                325                 330

<210> SEQ ID NO 9
<211> LENGTH: 993
<212> TYPE: DNA
<213> ORGANISM: Mus musculus

<400> SEQUENCE: 9
atgcgctcgc acactggcct gagggcgctt gtggcgcctg gttacccgct cctccttcta      60
tgtcttctgg cggcgacgcg ccctgatccg gctgagggcg atcccacaga tccaactttt    120
acaagtctac ctgttcgaga agaaatgatg gcgaaatact caaacctttc cttaaagagc    180
tgtaatatct cagtgacgga aaagtccaat gtatcagtag aagagaacgt aattttggaa    240
aagccttctc atgtggaact caaatgcgtg tacacagcaa ctaaggattt gaacttgatg    300
aatgtgactt ggaagaaaga tgatgagccc cttgagacta cgggtgactt caatacaact    360
aaaatgggca cacccttaac cagtcagtac aggttcatcg ttttttaatag caaacaattg    420 ggaaaatatt cttgtgtctt tggagaaaag gaactaagag ggacctttaa catccacgta    480
cccaaagctc atgggaaaaa aaagtcgttg atcgcttacg tgggggattc tactgtgctg    540
aagtgtgtat gtcaagattg tcttcctttta aattggactt ggtacatggg taatgaaacc    600
gcacaggttc ccattgacgc tcactcgaat gaaaagtata tcatcaatgg ttcccatgcc    660
aatgaaacaa ggctcaagat taagcatctt ttggaggaag atggaggatc ctactggtgt    720
cgtgccacct tccagttagg ggagagtgag gagcagaatg agctggttgt gctgagcttc    780
ctggtgcccc tcaagccatt tctggccata cttgccgaag tcatcctctt ggtggccatc    840
attctgcttt gtgaagtgta cacacacaag aaaaagaatg acccagatgc tgggaaagaa    900
tttgaacaaa ttgaacagct gaaatcagat gatagcaatg gcatagaaaa caatgtcccc    960
cggtacagaa aaactgactc tgcagatcag tga                                   993
```